US011674181B2

(12) United States Patent
Murphy et al.

(10) Patent No.: US 11,674,181 B2
(45) Date of Patent: *Jun. 13, 2023

(54) METHOD FOR IDENTIFYING KIDNEY ALLOGRAFT RECIPIENTS AT RISK FOR CHRONIC INJURY

(71) Applicants: Icahn School of Medicine At Mount Sinai, New York, NY (US); Western Sydney Local Health District, Westmead (AU)

(72) Inventors: Barbara Murphy, Pelham Manor, NY (US); Weijia Zhang, Cresskill, NJ (US); Philip J. O'Connell, Gladesville (AU)

(73) Assignees: Icahn School of Medicine at Mount Sinai, New York, NY (US); Western Sydney Local Health District, Westmead (AU)

( * ) Notice: Subject to any disclaimer, the term of this patent is extended or adjusted under 35 U.S.C. 154(b) by 130 days.

This patent is subject to a terminal disclaimer.

(21) Appl. No.: 17/164,607

(22) Filed: Feb. 1, 2021

(65) Prior Publication Data
US 2021/0230700 A1 Jul. 29, 2021

Related U.S. Application Data

(63) Continuation of application No. 15/125,009, filed as application No. PCT/US2015/020291 on Mar. 12, 2015, now Pat. No. 10,941,446.

(60) Provisional application No. 61/951,651, filed on Mar. 12, 2014.

(51) Int. Cl.
C12Q 1/68 (2018.01)
C12P 19/34 (2006.01)
C12Q 1/6883 (2018.01)

(52) U.S. Cl.
CPC ...... *C12Q 1/6883* (2013.01); *C12Q 2600/118* (2013.01); *C12Q 2600/158* (2013.01)

(58) Field of Classification Search
CPC ............ C12Q 1/6883; C12Q 2600/118; C12Q 2600/158
See application file for complete search history.

(56) References Cited

U.S. PATENT DOCUMENTS

| 6,582,908 | B2 | 6/2003 | Fodor et al. |
| 10,308,985 | B2 | 6/2019 | Murphy et al. |
| 10,787,709 | B2 | 9/2020 | Murphy et al. |
| 10,941,446 | B2 * | 3/2021 | Murphy ............... C12Q 1/6883 |
| 2006/0270612 | A1 | 11/2006 | Blatt et al. |
| 2007/0269827 | A1 | 11/2007 | Harley |
| 2008/0319027 | A1 | 12/2008 | Tao et al. |
| 2009/0022730 | A1 | 1/2009 | Raulf et al. |
| 2009/0191548 | A1 | 7/2009 | Berlin et al. |
| 2011/0144914 | A1 | 6/2011 | Harrington et al. |
| 2011/0171664 | A1 | 7/2011 | O'Brien |
| 2011/0189680 | A1 | 8/2011 | Keown et al. |
| 2011/0212090 | A1 | 9/2011 | Pedersen et al. |
| 2012/0003228 | A1 | 1/2012 | Smith et al. |
| 2012/0177645 | A1 | 7/2012 | Langermann et al. |
| 2012/0282696 | A1 | 11/2012 | Johnson et al. |
| 2012/0321614 | A1 | 12/2012 | Michaud et al. |
| 2013/0064835 | A1 | 3/2013 | Schmidt |
| 2013/0078633 | A1 | 3/2013 | Hutchins et al. |
| 2013/0131194 | A1 | 5/2013 | Skog et al. |
| 2013/0142728 | A1 | 6/2013 | Beaudenon-Huibregtse et al. |
| 2013/0143755 | A1 | 6/2013 | Sarwal et al. |
| 2013/0216533 | A1 | 8/2013 | Bais et al. |
| 2014/0045915 | A1 | 2/2014 | Skog et al. |
| 2014/0100124 | A1 | 4/2014 | Wylie et al. |
| 2014/0141986 | A1 | 5/2014 | Spetzler et al. |
| 2014/0329704 | A1 | 11/2014 | Melton et al. |
| 2015/0167085 | A1 | 6/2015 | Salomon et al. |
| 2017/0114407 | A1 | 4/2017 | Murphy et al. |
| 2017/0137883 | A1 | 5/2017 | Murphy et al. |
| 2017/0152560 | A1 | 6/2017 | Murphy et al. |
| 2018/0068057 | A1 | 3/2018 | Shin et al. |
| 2018/0356402 | A1 | 12/2018 | Fairchild et al. |
| 2019/0345556 | A1 | 11/2019 | Murphy et al. |
| 2022/0090197 | A1 | 3/2022 | Murphy et al. |

FOREIGN PATENT DOCUMENTS

| CN | 1518458 | 8/2004 |
| CN | 101039951 | 9/2007 |
| CN | 101360835 | 2/2009 |
| CN | 102099484 | 6/2011 |
| CN | 102119224 | 7/2011 |

(Continued)

OTHER PUBLICATIONS

Affymetrix NetAffx Search results. pp. 1-17, accessed Apr. 8, 2021 (Year: 2021).

Alakulppi et al., "Diagnosis of Acute Renal Allograft Rejection by Analyzing Whole Blood mRNA Expression of Lymphocyte Marker Molecules," Transplantation, Mar. 2007, 83: 791-798.

Allanach et al., "Comparing microarray versus RT-PCR assessment of renal allograft biopsies: Similar performance despite different dynamic ranges," American Journal of Transplantation, 2008, 8:1006-1015.

AU Office Action in Australian Appln. No. 2015229270, dated Jul. 9, 2020, 8 pages.

(Continued)

*Primary Examiner* — Stephen T Kapushoc
(74) *Attorney, Agent, or Firm* — Fish & Richardson P.C.

(57) ABSTRACT

A method for identifying a renal allograft recipient at risk for chronic allograft damage or interstitial fibrosis and tubular atrophy (IF/TA) by comparing the transcription level of a preselected gene signature set with the transcription level of a comparison standard, and diagnosing the recipient as being at risk for chronic allograft damage if the transcription level of the preselected gene signature set is significantly higher than the transcription level of the comparison standard.

11 Claims, No Drawings

(56) References Cited

FOREIGN PATENT DOCUMENTS

| | | |
|---|---|---|
| CN | 102186987 | 9/2011 |
| CN | 102597268 | 7/2012 |
| CN | 102666581 | 9/2012 |
| CN | 102712954 | 10/2012 |
| CN | 103025890 | 4/2013 |
| CN | 103421905 | 12/2013 |
| CN | 106461679 | 2/2017 |
| EP | 1374901 | 1/2004 |
| EP | 1731620 | 12/2006 |
| WO | WO 1996/039154 | 12/1996 |
| WO | WO 1997/003211 | 1/1997 |
| WO | WO 2001/081916 | 11/2001 |
| WO | WO 2004/074815 | 9/2004 |
| WO | WO 2007/104537 | 9/2007 |
| WO | WO 2009/143624 | 12/2009 |
| WO | WO 2010/083121 | 7/2010 |
| WO | WO 2011/127219 | 10/2011 |
| WO | WO 2011/143499 | 11/2011 |
| WO | WO 2012/174282 | 12/2012 |
| WO | WO 2013/063322 | 5/2013 |
| WO | WO 2013/063544 | 5/2013 |
| WO | WO 2013/079701 | 7/2013 |
| WO | WO 2013/079791 | 7/2013 |
| WO | WO 2014045915 | 3/2014 |
| WO | WO 2014/071205 | 5/2014 |
| WO | WO 2017/100259 | 6/2017 |
| WO | WO 2017/147196 | 8/2017 |
| WO | WO 2017/203008 | 11/2017 |

OTHER PUBLICATIONS

AU Office Action in Australian Appln. No. 2015279542, dated Aug. 28, 2020, 5 pages.
AU Office Action in Australian Appln. No. 2015279542, dated May 11, 2021, 3 pages.
AU Office Action in Australian Appln. No. 2015279621, dated Aug. 28, 2020, 4 pages.
Ben-Dov et al., "MicroRNA sequence profiles of human kidney allografts with or without tubulointerstitial fibrosis," Transplantation, Dec. 15, 2012, 94(11):1086-1094.
BR Office Action in Brazilian Appln. No. 112016030313-0, dated Dec. 10, 2019, 4 pages (English Translation Only).
BR Office Action in Brazilian Appln. No. 112016030360-1, dated Nov. 29, 2019, 5 pages (English Translation Only).
CA Office Action in Canadian Appln. No. 2942384, dated Mar. 11, 2021, 7 pages.
Chapman, "Do protocol transplant biopsies improve kidney transplant outcomes?," Curr Opin Nephrol Hypertens, Nov. 2012, 21:580-586.
Cheung et al., "Natural variation in human gene expression assessed in lymphoblastoid cells," Nature Genetics, Feb. 3, 2003, 33:422-425.
Cho et al., "Pirfenidone: an anti-fibrotic therapy for progressive kidney disease," Expert Opinion on Investigational Drugs, Feb. 2010, 19(2):275-283.
CN Office Action in Chinese Appln. No. 201580024911.0, dated Dec. 1, 2017, 17 pages (with English Translation).
CN Office Action in Chinese Appln. No. 201580045235.5, dated Jan. 16, 2020, 8 pages (English translation).
CN Office Action in Chinese Appln. No. 201580045324.X, dated Jan. 16, 2020, 7 pages (English translation).
CN Office Action in Chinese Appln. No. 201811063221.8, dated Jun. 1, 2021, 18 pages (with English Translation).
Cobb et al., "Sepsis gene expression profiling: Murine splenic compared with hepatic responses determined by using complementary DNA microarrays," Crit. Care Med., 2002, 30(12):2711-2721.
Cosio et al., "Predicting subsequent decline in kidney allograft function from early surveillance biopsies," American Journal of Transplantation, Oct. 2005,5:2464-2472.

Einecke et al., "A molecular classifier for predicting future graft loss in late kidney transplant biopsies," The Journal of Clinical Investigation, 2010, 120:1862-72.
El-Zoghby et al., "Identifying specific causes of kidney allograft loss," American Journal of Transplantation, Mar. 2009, 9:527-35.
EP Extended European Search Report in European Application No. 15761612.9, dated Aug. 2, 2017, 7 pages.
EP Extended European Search Report in European Application No. 15812651.6, dated Jan. 3, 2018, 9 pages.
EP Extended European Search Report in European Application No. EP110466HV, dated Feb. 1, 2018, 10 pages.
EP Office Action in European Application No. 15811195.5, dated Jul. 9, 2019, 4 pages.
Flechner et al., "Kidney transplant 1,2 rejection and tissue injury by gene profiling of biopsies and peripheral blood lymphocytes," American Journal of Transplantation, Sep. 2004, 4: 1475-1489.
Furness et al., "International variation in histologic grading is large, and persistent feedback does not improve reproducibility," Am J Surg Pathol, Jun. 2003, 27:805-810.
Gorantla et al., "Immunosuppressive agents in transplantation: mechanisms of action and current anti-rejection strategies," Microsurgery, Feb. 2000, 20:420-429.
Hai et al., "Changes of early response gene expression profile of peripheral lymphocytes in human renal allograft recipients," Journal of Clinical Rehabilitative Tissue Engineering Research, 2009, 13(5):841-844 (with English Abstract).
Hayry et al., "Protocol core needle biopsy and histological chronic allograft damage index as surrogate endpoint for Long-Term graft survival," Transplant Proc, Jan.-Feb. 2004, 36:89-91.
Hoshikawa et al., "Hypoxia induces different genes in the lungs of rats compared with mice," Physiol Genomics, Dec. 3, 2002, 12:209-219.
Irizarry et al., "Summaries of Affymetrix GeneChip probe level data," Nucleic Acids Research, 2003, 31:e15.
Isoniemi et al., "Histological chronic allograft damage index accurately predicts chronic renal allograft rejection," Transplantation, Dec. 1994, 58:1195-1198.
Johnson and Li, "Adjusting batch effects in microarray expression data using empirical Bayes methods," Biostatistics, 2007, 8:118-127.
Karczewski et al., "Cytometric analysis of TH1/TH2 cytokines in the urine of patients undergoing kidney transplantation," Annals of Transplantation, 2009, 14(3):25-28.
Kulkarni, Meghana M. "Digital multiplexed gene expression analysis using the NanoString nCounter system," Current Protocols in Molecular Biology, Apr. 1, 2011: 25B-10.1-25B10.17.
Kurtkoti et al., "The utility of 1- and 3-month protocol biopsies on renal allograft function: a randomized controlled study," American Journal of Transplantation, Feb. 2008, 8:317-23.
Li et al., "Fast and accurate short read alignment with Burrows-Wheeler transform," Bioinformatics, 2009, 25(14):1754-1760.
Li et al., "Identification of Common Blood Gene Signatures for the Diagnosis of Renal and Cardiac Acute Allograft Rejection," PLOS One, Dec. 2013, 8: e82153.
Malkov et al. "Multiplexed measurements of gene signatures in different analytes using the Nanostring nCounter Assay System" BMC Research Notes, May 9, 2009 (May 9, 2009), vol. 2, pp. 1-9. entire document.
Maluf et al., "The urine microRNA profile may help monitor post-transplant renal graft function," Kidney International, Jan. 1, 2014, 85(2):439-449.
Mannon et al., "Inflammation in areas of tubular atrophy in kidney allograft biopsies: a potent predictor of allograft failure," American Journal of Transplantation, 2010; 10:2066-73.
Meier-Kriesche et al., "Lack of improvement in renal allograft survival despite a marked decrease in acute rejection rates over the most recent era," American Journal of Transplantation, Jan. 2004, 4:378-83.
Mengel et al., "Banff 2011 Meeting report: new concepts in antibody-mediated rejection," American Journal of Transplantation, 2012, 12:563-570.

(56) References Cited

OTHER PUBLICATIONS

Menon et al., "Moving biomarkers toward clinical implementation in kidney transplantation," Journal of the American Society of Nephrology, 2017, 28:735-747.
Metzker, "Sequencing technologies—the next generation," Nature Reviews Genetics, Jan. 2010, 11:31-46.
Miller et al., "A new method for stranded whole transcriptome RNA-seq," Methods, 2013, 63(2):126-134.
Morgun et al., "Molecular profiling improves diagnoses of rejection and infection in transplanted organs," Circulation Research, 2006, 98(12):e74-e83.
Mueller et al., "Microarray analysis of rejection in human kidney transplants using pathogenesis-based transcript sets," American Journal of Transplantation., 2007, 7(2):2712-2722.
Naesens et al., "Progressive histological damage in renal allografts is associated with expression of innate and adaptive immunity genes," Kidney International, Dec. 2011,80:1364-76.
Nankivell et al., "Effect of histological damage on long-term kidney transplant outcome," Transplantation, Feb. 2001, 71:515-523.
Nankivell et al., "The natural history of chronic allograft nephropathy," N Engl J Med, 2003, 349:2326-33.
Nguyen et al. "Molecular Mechanisms Involved in Calcineurin Inhibitor Nephrotoxicity in Kidney Allograft Transplants," Master's Thesis, Virginia Commonwealth University, Aug. 8, 2011 (Aug. 8, 2011), pp. 1-74. Retrieved from the Internet<ttp://scholarscompass.vcu.edu/etd/2545/> on May 7, 2015 (May 7, 2015). entire document.
Omran et al., "MicroRNAs: New Insights into Chronic Childhood Diseases," BioMed Research International, Jul. 7, 2013, 2013:13 pages.
Park et al., "Fibrosis with inflammation at one year predicts transplant functional decline," J Am Soc Nephrol, 2010, 21:1987-97.
PCT International Preliminary Report on Patentability in International Application No. PCT/US2015/038147, dated Dec. 27, 2016, 10 pages.
PCT International Preliminary Report on Patentability in International Appln. No. PCT/US2019/027618, dated Oct. 20, 2020, 9 pages.
PCT International Search Report and Written Opinion in International Appln. No. PCT/US2015/020291, dated Jun. 11, 2015, 15 pages.
PCT International Search Report and Written Opinion in International Appln. No. PCT/US2019/027618, dated Jul. 10, 2019, 12 pages.
PCT International Search Report and Written Opinion in International Appln. No. PCT/US2015/038171, dated Dec. 8, 2015, 15 pages.
PCT International Search Report and Written Opinion in International Appln. No. PCT/US2015/038147, dated Oct. 23, 2015, 11 pages.
Ritchie et al., "*limma* powers differential expression analyses for RNA-sequencing and microarray studies," Nucleic Acids Research, 2015, 43(7):e47.
Rush et al., "Beneficial effects of treatment of early subclinical rejection: a randomized study," J Am Soc Nephrol, 1998, 9:2129-34.
Rush et al., "Lack of benefit of early protocol biopsies in renal transplant patients receiving TAC and MMF: a randomized study," American Journal of Transplantation, Nov. 2007, 7:2538-45.
Schadt et al., "A window into third-generation sequencing," Human Molecular Genetics, Sep. 21, 2010, 19(2):R227-R240.
Scherer et al., "Transcriptome changes in renal allograft protocol biopsies at 3 months precede the onset of interstitial fibrosis/tubular atrophy (IF/TA) at 6 months," Nephrol Dial Transplant, 2009, 24:2567-75.
Schwarz et al., "Safety and adequacy of renal transplant protocol biopsies," American Journal of Transplantation, Aug. 2005, 5:1992-6.
Seron et al., "Early protocol renal allograft biopsies and graft outcome," Kidney Int, Jan. 1997, 51:310-316.
Seron et al., "Reliability of chronic allograft nephropathy diagnosis in sequential protocol biopsies," Kidney Int, 2002, 61:727-33.
Shendure et al., "Next-generation DNA sequencing," Nature Biotechnology, 2008, 26(10):1135-1145.
Shishido et al., "The impact of repeated subclinical acute rejection on the progression of chronic allograft nephropathy," J Am Soc Nephrol, 2003, 14:1046-52.
Solez et al., "Banff 07 classification of renal allograft pathology: updates and future directions," American Journal of Transplantation, 2008, 8:753-760.
Spector et al., "Development and Validation of a MicroRNA-Based Diagnostic Assay for Classification of Renal Cell Carcinomas," Molecular Oncology, Mar. 26, 2013, 7:732-738.
Spivey et al., "Gene expression profiling in acute allograft rejection: challenging the immunologic constant of rejection hypothesis," Journal of Translational Medicine, 2011, 9:1-22.
Stegall et al., "The histology of solitary renal allografts at 1 and 5 years after transplantation," American Journal of Transplantation, Apr. 2011, 11:698-707.
Subramanian et al., "Gene set enrichment analysis: a knowledge-based approach for interpreting genome-wide expression profiles," PNAS, Oct. 2005, 102:15545-50.
Wolfe et al., "Trends in organ donation and transplantation in the United States, 1999-2008," American Journal of Transplantation, Apr. 2010, 10:961-72.
Yilmaz et al, "Clinical predictors of renal allograft histopathology: a comparative study of single-lesion histology versus a composite, quantitative scoring system," Transplantation, Mar. 2007, 83:671-676.
Yilmaz et al., "Protocol core needle biopsy and histologic Chronic Allograft Damage Index (CADI) as surrogate end point for long-term graft survival in multicenter studies," Journal of the American Society of Nephrology, 2003, 14:773-779.
Zhang et al., "Pretransplant transcriptomic signature in peripheral blood predicts early acute rejection," JCI Insight. 2019, 4(11):e127543.
Gökmen-Polar et al., "Elevated protein kinase C $\beta$II is an early promotive event in colon carcinogenesis," Cancer Research, 2001, 61(4):1375-1381.
Haynes et al., "Proteome analysis: Biological assay or data archive?," Electrophoresis, 1998, 19(11):1862-1871.
NCBI [Online], "NCBI GEO Platform GPL570—Affymetrix Human Genome U133 Plus 2.0 Array," Nov. 7, 2003, [Retrieved on Jun. 10, 2022], retrieved from URL<ncbi.nlm.nih.gov/geo/query/acc.cgi?acc=GPL570>, 4 pages.
Tuttle et al., "Placental lactogen is expressed but is not translated into protein in breast cancer," PLOS ONE, 2014, 9(1):e87325.
Alakulppi et al., "Diagnosis of Acute Renal Allograft Rejection by Analyzing Whole Blood mRNA Expression of Lymphocyte Marker Molecules," Transplantation, Mar. 2007, 83(6):791-798.
Bontadini, "HLA techniques: Typing and antibody detection in the laboratory of immunogenetics," Methods, Apr. 2012, 56(4):471-576.
BR Office Action in Brazilian Appln. No. 112016020987-7, dated Oct. 8, 2019, 5 pages (English Translation Only).
CA Office Action in Canadian Appln. No. 2953368, dated May 4, 2021, 4 pages.
CA Office Action in Canadian Appln. No. 2953369, dated May 3, 2021, 4 pages.
Chen et al., "Changes of early response gene expression profile of peripheral lymphocytes in human renal allograft recipients," Journal of Clinical Rehabilitative Tissue Engineering Research, Jan. 29, 2009, 13(5):841-844 (with English abstract).
CN Office Action in Chinese Appln. No. 201580045324.X, dated Dec. 24, 2020, 10 pages (with English translation).
EP Office Action in European Application No. 15812651.6, dated Oct. 10, 2019, 5 pages.
Hurvich et al., "A Corrected Akaike Information Criterion for Vector Autoregressive Model Selection," Journal of Time Series Analysis, 2008, 14:271-279.
Ihaka, "R: A Language for Data Analysis and Graphics," Journal of Computational and Graphical Statistics, Sep. 1996, 5(3):299-314.
Li et al., "The Sequence Alignment/Map format and SAMtools," Bioinformatics. Aug. 2009; 25(16): 2078-2079.

(56) References Cited

OTHER PUBLICATIONS

Mata et al., "A Hexameric Phosphorothioate Oligonucleotide Telomerase Inhibitor Arrests Growth of Burkitt's Lymphoma Cells in Vitro and in Vivo," Toxicology Appl.ied Pharmacology, May 1997, 144:189-197.

Mootha et al., "PGC-1alpha-responsive genes involved in oxidative phosphorylation are coordinately downregulated in human diabetes," Nat Genet, 2003, 34:267-273.

Samstag et al., "Synthesis and Properties of New Antisense Oligodeoxynucleotides Containing Benzylphosphonate Linkages," Antisense Nucleic Acid Drug Development, 1996, 6:153-156.

Strauss-Soukup et al., "Effects of Neutralization Pattern and Stereochemistry on DNA Bending by Methylphosphonate Substitutions," Biochemistry, Jul. 1997, 36:8692-8698.

Tibshirani et al., "Regression Shrinkage and Selection via the Lasso," Journal of the Royal Statistical Society Series B, 1996, 58:267-288.

Tran et al., "Inferring causal genomic alterations in breast cancer using gene expression data," BMC Syst Biol, Aug. 2011, 5:121.

Trapnell et al., "Differential gene and transcript expression analysis of RNA-seq experiments with TopHat and Cufflinks," Nat Protoc, Mar. 2012, 7:562-578.

Vahed et al., "Diagnosis of Interstitial Fibrosis and Tubular Atrophy in Kidney Allograft: Implementation of MicroRNAs ", Iranian Journal of Kidney Diseases, Jan. 2014, 8(1):4-12.

Zhu et al., "Integrating large-scale functional genomic data to dissect the complexity of yeast regulatory networks," Nat Genet, Jul. 2008, 40:854-861.

CA Office Action in Canadian Appln. No. 2953369, dated Apr. 6, 2022, 3 pages.

EP Extended European Search Report in European Application No. 19789535.2, dated Mar. 10, 2022, 16 pages.

EP Partial Search Report in European Application No. 19789535.2, dated Dec. 6, 2021, 17 pages.

CA Office Action in Canadian Appln. No. 2942384, dated Jan. 14, 2022, 5 pages.

U.S. Appl. No. 15/125,009, filed Sep. 9, 2016, Barbara Murphy.
U.S. Appl. No. 15/321,885, filed Dec. 23, 2016, Barbara Murphy.
U.S. Appl. No. 15/320,208, filed Dec. 19, 2016, Barbara Murphy.
U.S. Appl. No. 16/424,014, filed May 28, 2019, Barbara Murphy.
U.S. Appl. No. 17/046,692, filed Oct. 9, 2020, Barbara Murphy.

\* cited by examiner

METHOD FOR IDENTIFYING KIDNEY ALLOGRAFT RECIPIENTS AT RISK FOR CHRONIC INJURY

CROSS-REFERENCE TO RELATED APPLICATIONS

This application is a continuation, and claims priority, of U.S. application Ser. No. 15/125,009, having a 371 completion date of Sep. 9, 2016, now U.S. Pat. No. 10,941,446, issued Mar. 9, 2021, which is a U.S. National Stage application, and claims priority of International Application No. PCT/US2015/020291, filed Mar. 12, 2015, which claims priority of U.S. Provisional Application Ser. No. 61/951,651, filed Mar. 12, 2014. The contents of all of the prior applications are incorporated herein by reference in their entirety.

FIELD OF THE INVENTION

The present invention pertains to methods for identifying kidney allograft recipients at risk for chronic injury and a kit for use in the invention. The methods comprise analyzing transcriptome signatures obtained from early biopsies of stably functioning kidney allografts in order to identify and treat such patients.

BACKGROUND OF THE INVENTION

Kidney transplantation is the most common solid organ transplant performed in the US; more than 16,000 transplants were performed in 2010 (2011 SRTR data report). Despite a reduced incidence of acute rejection, improvements in long-term allograft survival have not been realized (1-2).

Chronic allograft damage (CAD), or interstitial fibrosis and tubular atrophy (IF/TA) of unknown cause is the major determinant of graft loss after the first year of transplantation (3). Clinical and histological events associated with IF/TA are poorly predictive of graft loss (4), making it difficult to identify allografts which may benefit from early interventions to prevent progression of fibrosis. Allograft biopsies in response to renal dysfunction remain the current diagnostic approach to chronic injury, by which stage irreversible fibrosis has developed. There is substantial evidence that pathological changes in the renal allograft predate functional changes (5). Protocol biopsies have suggested that upwards of fifty percent of grafts with stable renal function have evidence of IF/TA by 1 year (6). The development of a predictive assay to identify at risk grafts early after transplantation is essential to design targeted therapeutic interventions. The present inventors have learned that molecular changes obtained from protocol biopsies conducted early after transplantation predate the development of fibrosis. Pursuant to the present invention, a predictive gene set has been developed that identifies allografts at risk of progressive injury. This finding enables the identification of recipients at risk of graft loss at a time when therapeutic intervention may prevent IF/TA.

SUMMARY OF THE INVENTION

A 13 gene set has been identified that is independently predictive for the development of fibrosis at 1 year and early graft loss. The high predictive capacity of the gene set (AUC 0.947) was superior to clinical indicators (AUC 0.78). Routine histological parameters failed to identify histologically normal allografts in which fibrosis progressed, while the predictive gene set accurately discriminated and identified histologically normal allografts in which fibrosis ultimately progressed (AUC=0.987). The 13-genes also predicted early graft loss accurately (AUC-0.86 & 0.83 at 2- & 3-yrs respectively). The predictive value of this gene set was validated using an independent cohort and two independent, publicly available, expression datasets.

The gene set obtained at 3 months from stably functioning renal allografts correlated with the progression of established markers for chronic allograft damage at 12 months and proved superior to clinico-pathological variables currently used in clinical practice to identify renal transplant recipients at risk of allograft damage and loss.

In one aspect, the present invention provides a method for identifying a kidney allograft recipient at risk for chronic allograft damage comprising the steps of providing a biopsy specimen from a renal allograft obtained at 3 months post transplantation.

In a further aspect, the present invention provides primers for a selected 13 gene signature set comprising the genes KLHL13, KAAG1, MET, SPRY4, SERINC5, CHCHD10, FJX1, WNT9A, RNF149, ST5, TGIF1, RXRA and ASB15.

In a further aspect the invention provides a method of selecting a renal allograft recipient for treatment to reduce the risk of chronic allograft damage or IF/TA by comparing the transcription level of a preselected gene signature set obtained from the allograft with the transcription level of a comparison expression library, and selecting the patient for treatment for allograft rejection or damage if the transcription level of the preselected gene signature set is significantly higher than the transcription level of the comparison standard.

In another aspect the invention provides a gene signature set for identifying patients at risk for chronic renal damage or IF/TA comprising the genes KLHL13, KAAG1, MET, SPRY4, SERINC5, CHCHD10, FJX1, WNT9A, RNF149, ST5, TGIF1, RXRA and ASB15.

In a still further aspect, the present invention provides a kit for identifying renal allograft recipients at risk for chronic allograft damage comprising in separate containers comprising primers for a 13 member gene signature set, buffers, three housekeeping genes and negative controls and instructions for use.

These and other aspects of the present invention will be apparent to those of ordinary skill in the art in light of the present specification, claims and drawings.

DETAILED DESCRIPTION OF THE INVENTION

Definitions

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

Disclosed herein is a prospective study of serial protocol biopsies at predefined time points with unique and detailed clinical, histological, and molecular data sets. A gene set (the gene signature set, KLHL13, KAAG1, MET, SPRY4, SERINC5, CHCHD10, FJX1, WNT9A, RNF149, ST5, TGIF1, RXRA, ASB15) obtained at 3 months post transplantation from stably functioning renal allografts has been identified and validated. This gene set can be used to predict the progression of chronic allograft damage. This molecular risk gene signature has been found to be superior to clinico-pathological variables in identifying renal transplant recipients at risk for histological progression to graft injury in several patient cohorts and graft loss in a publically available cohort. The present invention provides a method for identifying renal allograft recipients at risk for chronic allograft injury which employs a selected gene signature set as described herein. Allograft recipients having an increased expression of the 13 member signature set are at risk for chronic allograft injury. The present invention provides materials and methods to identify such patients as set forth herein.

The natural history of chronic allograft injury has revealed an early and rapid histological deterioration by 12-months post transplant (3). The presence of adverse histological changes (fibrosis and/or inflammation) at 12-months was then correlated with adverse long-term allograft outcomes in standard- and low-risk kidneys (14-16). Specifically, a Chronic Allograft Damage Index score at 12 months (CADI-12) of ≥2 has identified recipients at risk for graft loss at 3-years in the cohort described herein, and from prior publications (5, 17). Owing to the more gradual histological deterioration observed in allografts after 12-months, interventions in immunotherapy once chronic allograft damage is established are less likely to alter outcomes (3).

While earlier time-point allograft histology has been correlated with the progression of Chronic Allograft Neuropathy (CAN) and allograft loss (18), clinico-pathologic variables that classify allografts into those at-risk for early histological deterioration and later graft loss, with even moderate sensitivity, have not been identified. For instance, while 60% of the cohort had low CADI scores (0-1) at 3 months, more than half of the patients with histological progression of allograft damage by 12-months belonged to this group, and were unidentifiable at 3-months by histology alone. Progression of Banff scores (6) within the first year without detectable changes in creatinine have also been noted (19). Conversely, histological changes observed at 3 months have been reported to reverse by 12-month assessments (20).

In the cohort disclosed herein, 40% of allografts with high CADI-3 had improved to CADI-12 of 0-1. Therefore, a significant clinical application of the 13-member gene signature set of the present invention is the ability to identify kidneys at risk for CAN development and progression, currently not identifiable by clinico-pathological parameters alone, at a stage when they are amenable to interventions. Furthermore, as opposed to a "one size fits all" immunosuppression strategy, the gene set herein has the potential to stratify low-risk allograft recipients who may then benefit from lowered immunosuppression.

As has been shown by many groups, the causes of chronic kidney allograft injury are diverse and cumulative (3, 15). This is reflected in the relatively large number of genes that were associated with adverse allograft outcomes in the 2 prior art validation cohorts. Einecke et al, identified a tissue gene signature (886 genes related to tissue injury, TGF-β effects) that was predictive of graft loss in for-cause allograft biopsies performed between 1-31 years post transplant8. A 601 probe-set signature from 6-month protocol biopsies in low-risk pediatric recipients, showed upregulation of immune response genes in patients who had histologic progression compared to those who did not (9). The 13-gene signature set of the present invention was validated with high predictive value in all of these cohorts with an ability to predict allograft outcomes despite differences in demographics, timing of biopsies post-transplant, presence of preexisting fibrosis and the respective endpoint studied (Table 9).

Additionally, these two prior art studies used a limited gene set based on previous data or predicted pathological pathways. In contrast, an all-inclusive, non-hypothesis driven approach facilitated by sample size and based on the multifaceted nature of chronic injury was taken. Since CADI-12m is an ordinal variable, the initial gene list was derived based upon a signal of correlation, higher gene expression at 3-months and correlation with CADI-12, rather than a comparison between gene-expression in 2 well-defined clinical cohorts, as in previous studies. The method of the present invention increases the robustness of the identified relation and enhances the clinical application in undefined cohorts.

The addition of clinical predictors predictive of high CADI-12 (donor age, recipient gender, deceased donor organ, and acute rejection within 3 months of transplant) did not significantly enhance the performance of the gene set in predicting CAN. Subclinical rejection, predominantly borderline, was present in 20 of the 3 month biopsies. Additional analysis in which patients with acute cellular rejection (ACR) or i+t (the combined score for inflammation (i) and tubulitis (t))>2 were excluded clearly demonstrated that inflammation was not the predominant driver for the identified 13-gene signature set with the AUC remaining 1 (data not shown). The novel, non-biased approach used herein has thus identified a risk gene signature that differentiates allografts at risk for histological progression in the cohort. This invention bears wider applicability to identify at-risk kidneys as suggested by its validation in predicting allograft injury and failure in a variety of patient cohorts in whom biopsies taken at different time points post-transplant with and without pre-existing damage.

Protocol biopsies on stably functioning allografts provide a window into pathogenetic mechanisms that are initiated prior to the development of detectable allograft dysfunction. Ongoing subclinical rejections, polyomavirus BK infection, Calcineurin Inhibitor (CNI)-toxicity and antibody-mediated damage—processes that contribute to CAN which when detected can be intervened upon—may be identified (24-26). However, other studies have been unable to demonstrate significant differences in allograft outcomes with interventions performed on detected subclinical phenomena (27). This disparity may reflect the limitations of using histology alone while interpreting protocol biopsies, which may be influenced by inter-observer and sampling variability. On the other hand, 3- and 6-month protocol biopsy transcriptome changes that correlated with allograft histology at 12-months (11, 28), and a 12-month allograft gene signature that was correlated with allograft loss (15), have all been reported. As disclosed herein the genes whose expressions correlated with 3- or 12-month CADI were identified by Spearman correlations analysis and then were subjected to overall Gene Ontology enrichment. The Gene Ontology (GO) functions/pathways associated with CADI-correlated genes from correlation analysis were also validated with Gene Set Enrichment Analysis (GSEA) (9).

In one embodiment, the present invention is directed to primers for RT-PCR for the 13 member gene signature sequence. In another embodiment, the present invention is directed to a kit for identifying allograft recipients at risk for renal allograft injury comprising a container having therein primers for RT-PCR for a 13 member gene signature set and instructions for use. In a further embodiment the kit comprises a first container having therein primers for RT-PCR for a 13 member gene signature, a second container having therein primers for housekeeping genes, a third container having therein a buffer solution and instructions for use. Patients are stratified based on expression and those with high expression of the 13 gene signature set are diagnosed as being at risk for chronic allograft damage, and are thereafter treated to prevent such damage. Pursuant to the present invention, patients with high expression of the 13 genes can be identified using, for example, Real Time PCR, Nanostring or miSeq. In each case a standard is generated as the baseline for identifying patients at risk for chronic allograft damage or IF/TA.

Determination of Diagnostic Cut Off Using RT-PCR, Nanostring and miSeq

Using a training set of patients, mRNA from the biopsy sample will be analyzed for expression levels of the 13 gene signature set. Based on this expression data, a mathematical model will be developed to estimate the probability of patient developing fibrosis by one year.

Patients will be stratified based on this score sensitivity/specificity, the positive predictive values (PPV) and negative predictive values (NPV) determined. Based on the PPV and the NPV an optimal cut off will be established which best categorizes the patients' risk for rejection. This may be a clear cut off into two groups in that if they are in the top group their expression levels are significantly higher and they have a high likelihood of developing fibrosis and the test is determined to be positive but if they are in the bottom they have a very low likelihood of developing fibrosis and the test is determined to be negative. In an alternative embodiment, the patients may be broken into tertiles based on their probability score determined as above. In this case if the patient is in (1) the top tertile, their expression levels are significantly higher and they have a high likelihood of developing fibrosis and the test is determined to be positive; (2) if they are in the second tertile or intermediate group their risk cannot be accurately determined; and (3) if they are in the bottom tertile they have a very low likelihood of developing fibrosis. and the test is determined to be negative.

The RT-PCR assay kit includes:

1) Primer container (16 tubes with one qPCR assay per tube for 16 genes including the 13-panel gene signature set of the present invention and housekeeping genes (ACTB and GAPDH) and the control probe 18s). The assays were purchased from LifeTech. The primers are set forth below.

| Primers for qPCR assay Assay ID (LifeTech ®) | Availability | Gene Symbol(s) |
|---|---|---|
| Hs99999901_s1 | — | 18s rRNA |
| Hs01060665_g1 | INV* | ACTB |
| Hs02758991_g1 | INV | GAPDH |
| Hs01067640_m1 | INV | RXRA |
| Hs00243321_m1 | INV | WNT9A |
| Hs00534909_s1 | INV | FJX1 |
| Hs01006506_m1 | INV | KLHL13 |
| Hs00698334_m1 | INV | SERINC5 |
| Hs01935412_s1 | INV | SPRY4 |
| Hs00704044_s1 | INV | KAAG1 |

-continued

| Primers for qPCR assay Assay ID (LifeTech ®) | Availability | Gene Symbol(s) |
|---|---|---|
| Hs01565584_m1 | INV | MET |
| Hs00395880_m1 | INV | ASB15 |
| Hs00936461_m1 | INV | ST5 |
| Hs01369775_g1 | INV | CHCHD10 |
| Hs00411860_m1 | INV | RNF149 |
| Hs00820148_g1 | INV | TGIF1 |

2) TaqMan ® Universal Master Mix II: reagents for qPCR reactions
3) TaqMan ® ARRAY 96-WELL PLATE 6x16
4) Agilent AffinityScript QPCR cDNA Synthesis Kit: for the highest efficiency conversion of RNA to cDNA and fully optimized for real-time quantitative PCR (QPCR) applications
*INV = Inventory Experimental Procedure and Data Analysis:

Total RNA will be extracted from the allograft biopsy samples using Allprep kit (QIAGEN-ALLprep kit, Valencia, Calif. USA). cDNA will be synthesized using the AffinityScript RT kit with oligo dt primers (Agilent Inc. Santa Clara, Calif.). TaqMan qPCR assays for the 13 gene signature set, 2 house-keeping genes (ACTB, GAPDH) and 18s are purchased from ABI Life Technology (Grand Island, N.Y.). qPCR experiments will be performed on cDNA using TAQMAN universal mix and the PCR reactions will be monitored and acquired using an ABI7900HT system. Samples will be measured in triplicate. Cycle Times (CT) values for the 13 member signature gene set as well as the 2 housing genes will be generated. The ΔCT value of each gene will be computed by subtracting the average CT value for the house-keeping genes from the CT value of each gene and a penalized logistic regression fitting model using an logistf R package will be then applied on ΔCT values to derive the statistical model from which the probability score of high for each patient will be calculated.

$$\log\frac{p(x)}{1-p(x)} = \beta_{0+}^* \beta_1^* g_1 + \beta_i^* g_i + \ldots + \beta_{13}^* g_{13}$$

where (p(x) is the probability of high CADI, $\beta^*_i$ is penalized coefficient and gi is the expression ΔCT of gene i)

Based on the probability score, prediction AUC, sensitivity/specificity, the positive (PPV) and negative predictive values (NPV) determined will determined. At a given specificity (90%), an optimal cut off will be established which best categorizes the patients risk for kidney fibrosis.

Example A

An independent cohort of 45 cohort patients (18: CADI≥2, and 27: CADI<2) was used as the training set for qPCR assay. The RNA samples were extracted and subjected to qPCR experiments using this qPCR assay kit. After data acquisition and normalization, a penalized logistic model with following β values (Table 1A) was built and the prediction AUC on the training set was 0.866. The statistical model based on the training set will be used to predict the probability of kidney fibrosis for new samples and the probability score cutoff is 0.548 at 90% specificity.

TABLE 1A

Parameters for penalized logistic regression model from qPCR training set

|  | β | sd (β) | lower95 | upper95 | Chisq |
|---|---|---|---|---|---|
| (Intercept) | −0.365 | 5.499985 | 11.1826 | 10.41205 | 0.005216 |
| KLHL13 | 0.121359 | 0.121611 | 0.06046 | 0.514791 | 1.642695 |
| MET | −0.31735 | 0.247157 | 0.93868 | 0.066704 | 2.564086 |
| KAAG1 | 0.279196 | 0.532691 | 0.75299 | 1.40152 | 0.266769 |
| SERINC5 | 0.110388 | 0.492916 | −0.785 | 1.022298 | 0.06097 |
| CHCHD10 | 0.594793 | 0.513221 | 0.32058 | 1.637405 | 1.58411 |
| SPRY4 | −0.39334 | 0.721153 | 2.26251 | 0.839415 | 0.349045 |
| FJX1 | 0.204501 | 0.33905 | 0.43074 | 0.932129 | 0.403804 |
| RNF149 | 0.06954 | 0.457496 | 0.73284 | 0.898595 | 0.03126 |
| ST5 | 0.740591 | 0.767047 | 0.48276 | 2.930863 | 1.272416 |
| TGIF1 | −0.40004 | 0.454692 | 1.32842 | 0.344652 | 1.089256 |
| RXRA | −0.28701 | 0.237485 | 0.76594 | 0.099958 | 2.098098 |
| ASB15 | −0.23106 | 0.173426 | −0.6974 | 0.062775 | 2.251056 |

Nanostring Assay Kit:
Nanostring assay kit includes:
1) Custom CodeSet (barcoded probe sets for 13 gene panel including 3 house-keeping genes and negative controls provided by Nanostring) Pack
2) nCounter® Master Kit including nCounter Cartridge, nCounter Plate Pack and nCounter Prep Pack
3) QIAGEN RNeasy® Kit for extraction of high quality total RNA Nanostring Experiments:
The total RNA will be extracted using QIAGEN RNeasy® Kit by following the manufacturer's protocol; Barcode probes will be annealed to the total RNA in solution at 65° C. with the master kit. The capture probe will capture the target to be immobilized for data. After hybridization, the sample will be transferred to the nCounter Pre Station and the probe/target will be immobilized on the nCouter Cartridge and the probes are then counted by the nCounter Digital Analyzer.

mRNA Transcriptomic Data Analysis
The raw count data from Nanostring analyzer will be processed in the following procedure the raw count data will be firstly normalized to the count of the house-keeping genes and the mRNAs with counts lower than the median plus 3 standard deviation of the counts of negative controls will be filtered out. Due to data variation arising from reagent lot, the count for each mRNA from different reagent lots will be calibrated by multiplying a factor of the ratio of the averaged counts of the samples on different reagent lots. The calibrated counts from different experimental batches will be further adjusted by ComBat package.

A penalized logistic regression fitting model using logistf R package will then be applied on normalized count values to derive the statistical model from which the probability score for each patient will be calculated.

The raw count data from the Nanostring analyzer will be processed in the following procedure: the raw count data will be first normalized to the count of the house-keeping genes and the mRNAs with counts lower than the median plus 3 standard deviation of the counts of negative controls will be filtered out. Due to data variation arising from reagent lot, the count for each mRNA from different reagent lots will be calibrated by multiplying a factor of the ratio of the averaged counts of the samples on different reagent lots. The calibrated counts from different experimental batches will be further adjusted by ComBat package.

A penalized logistic regression fitting model using logistf R package will be then applied on normalized count values to derive the statistical model from which the probability score of high likelihood for each patient will be calculated.

$$\log \frac{p(x)}{1-p(x)} = \beta^*_{0+}\beta^*_1 g_1 + \beta^*_i g_i + \ldots + \beta^*_{13} g_{13}$$

where (p(x) is the probability of high CADI, $\beta^*_i$ is penalized coefficiency and gi is the count of gene i)

Based on the probability score, prediction AUC, sensitivity/specificity, the positive (PPV) and negative predictive values (NPV) will be determined. At a given specificity (90%), an optimal cut off will be established which best categorizes the patients risk for kidney fibrosis. This may be a clear cut off into two groups in that if they are in the top group they have a high likelihood of developing fibrosis and the test is determined to be positive but if they are in the bottom they have a very low likelihood of developing fibrosis and the test is determined to be negative. The alternative is that patients may be broken in to tertiles based on the above their probability score determined as above. In this case if the patient is in (1) the top tertile they have a high likelihood of developing fibrosis and the test is determined to be positive; (2) they are in the second tertile or intermediate group their risk cannot be accurately determined; and (3) they are in the bottom they have a very low likelihood of developing fibrosis and the test is determined to be negative.

MiSEQ Experiments:
MiSEQ assay kit will include:
1) Custom Assay (barcoded probe sets for 13 gene panel including 5 house-keeping gene panel)
2) Illumina® TruSeq® RNA Sample Preparation Kit v2
3) QIAGEN RNeasy® Kit for extraction of high quality total RNA MiSEQ Experiments:
Total RNA will be extracted using QIAGEN RNeasy® Kit. The sequencing library will be generated using Illumina® TruSeq® RNA Sample Preparation Kit v2 by following manufacturer's protocol: briefly, polyA-containing mRNA will be first purified and fragmented from the total RNA. The first-strand cDNA synthesis will be performed using a random hexamer primer and reverse transcriptase followed by the second strand cDNA synthesis. After the end repair process, which converts the overhangs into blunt ends of cDNA, multiple indexing adapters will be added to the end of the double stranded cDNA. Next, PCR will be performed to enrich the targets using the primer pairs specific for the gene panel and house-keeping genes. Finally, the indexed libraries will be validated, normalized and pooled for sequencing on the MiSEQ sequencer.

mRNA Transcriptomic Data Analysis

The raw RNAseq data generated by MiSEQ sequencer will be processed using the following procedure: The reads with good quality will be firstly aligned to several human reference databases including hg19 human genome, exon, splicing junction and contamination database including ribosome and mitochondria RNA sequences using the well-known BWA alignment algorithm. After filtering reads mapped to the contamination database, the reads that are uniquely aligned with a maximal 2 base mis-matches to the desired amplicon regions will be then counted as expression level for the corresponding gene and further subjected to quantile normalization across samples after log 2 transformation A penalized logistic regression fitting model using logistf R package will be then applied on normalized count values to derive the statistical model from which the probability score of high likelihood for each patient will be calculated.

$$\log\frac{p(x)}{1-p(x)} = \beta^*_{0+}\beta^*_1 g_1 + \beta^*_i g_i + \ldots + \beta^*_{13} g_{13}$$

(where $p(x)$ is the probability of high CADI, $\beta^*_i$ is penalized coefficiency and $g_i$ is the count of gene i). Based on the probability score, prediction AUC, sensitivity/specificity, the positive (PPV) and negative predictive values (NPV) will be determined. At a given specificity (90%), an optimal cut off will be established which best categorizes the patients risk for kidney fibrosis. This may be a clear cut off into two groups in that if they are in the top group they have a significantly higher transcription level of the 13 member gene signature set and have a high likelihood of developing fibrosis and the test is determined to be positive but if they are in the bottom they have a very low likelihood of developing fibrosis and the test is determined to be negative. The alternative is that patients may be broken in to tertiles based on the above their probability score determined as above. In this case if the patient is in (1) the top tertile they have a significantly higher transcription level of the 13 member gene signature set and a high likelihood of developing fibrosis and the test is determined to be positive; (2) they are in the second tertile or intermediate group their risk cannot be accurately determined; and (3) they are in the bottom they have a very low likelihood of developing fibrosis and the test is determined to be negative.

The development of a predictive gene set that identifies those patients early after transplantation who are at increased risk of progressive graft injury has several applications: individualizing therapy based on risk profile including targeting "at-risk" individuals for early intervention and minimizing therapy in those with good prognosis. In addition, it can be used for risk stratification in clinical trials allowing for novel therapeutic regimens to be tested in targeted populations.

In summary, a gene signature from protocol biopsies of stably functioning renal allografts at 3-months has been developed and validated. The gene signature identifies kidney allograft recipients at risk for histological deterioration and functional decline by 12-months. This gene signature was externally validated to predict allografts that sustained diverse adverse outcomes, representing kidneys-at-risk in the intermediate and long term. The gene signature also has the potential to identify lower risk allograft recipients who may benefit from less intense The present invention is directed to methods for identifying kidney allograft recipients who are at risk for developing chronic allograft injury, expressed as interstitial fibrosis and tubular atrophy (IF/TA). Patients can be monitored at 3, 6, 9, 12 months, and yearly thereafter. When patients are identified as being at risk for developing chronic allograft injury, the present invention includes methods for treating such patients. Treatment approaches would be as follows: in patients identified as high risk for chronic allograft fibrosis with low immunological risk as determined by parameters including absence of the acute rejection, subclinical rejection including boarderline sublinical rejection on biopsy as defined by Banff Criteria (American Journal of Transplantation 2008; 8: 753-760), donor specific antibodies, and a low calculated Panel Reactive Antibodies (PRA—a measure of anti HLA antibodies), the methods include, without limitation, withdrawal of the calcineurin inhibitor (CNI), such as cyclosporine or tacrolimus, and substitution with a less fibrogenic immunosuppressive drug such as belatacept or sirolimus; and, in those patients identified as high risk for chronic allograft fibrosis with subclinical rejection including boarderline sublinical rejection on biopsy as defined by Banff Criteria (American Journal of Transplantation 2008; 8: 753-760), since subclinical rejection can contribute to the development of fibrosis, the methods include, without limitation, increase in immunosuppression such as an increase in the dose of calcineurin inhibitor (CNI), such as cyclosporine or tacrolimus or addition of another agent such as prednisone or mycophenolate mofetil.

In addition, patients that are identified as being at risk for developing chronic allograft injury can be treated with anti-fibrotic agents such as Pirfenidone, relaxin, Bone morphogenetic protein 7 (BMP-7), Hepatic growth factor (HGF) 6.

The present invention is described below using examples which are intended to further describe the invention without limiting the scope thereof.

In the examples below, the following materials and methods were used.

Patient Population and Biopsy Specimens

Exclusion criteria for patients described herein included a positive TB-CDC cross-match, desensitization for donor-specific antibodies, pediatric recipients and inability to give consent. Protocol renal allograft biopsies were obtained at 0, 3, 12, and 24 months post-transplant in 3 sites, and 0 and 24 months in 2 sites. Three-month protocol biopsies were performed on 244 patients, 204 of which had a corresponding 12-month biopsy. Microarray was performed on the first 159 3-month protocol biopsies hereinafter "m3_Bx") and the remaining 45 were used for validation.

Data Collection

Donor and recipient data was collected at baseline. Donor information included donor age, race, gender, HLA, cause of death, status living versus deceased (SCD, ECD, or DCD). Recipient data included age, gender, race, cause of End Stage Renal Disease (ESRD) HLA, PRA, anti-HLA antibodies, Cold Ischemic Time (CIT), Delayed Graft Function (DGF), induction and maintenance immunosuppression, cytomegalovirus (CMV) status, Hepititis C virus (HCV) and Hepititis B virus (HBV) status, duration 3, 6, 12 and 24 months, including physical exam, current infections, lab results (CBC, BUN, creatinine, metabolic panel and immunosuppression levels). In addition, clinical data were collected when a clinically indicated biopsy was performed.

HLA Antibody Screening

Serum was assayed for circulating anti-HLA antibodies at baseline using One Lambda Labscreen® beads (One Lambda Inc, Canoga Park, Calif.). A Mean Fluoroscence Intensity (MFI)>1000 was considered positive. The samples were analyzed on a Luminex Lab Scan 200™ using HLA Fusion software. Donor specific antibodies (DSA) were determined using the donor and recipient HLA typing. Patients with preformed DSA requiring desensitization protocols prior to or at the time of transplant were excluded from the study.

Histopathology and Diagnostic Classification

Two tissue cores were taken from each of the 3-month and 1 year protocol renal biopsies of the study cohort. One core was processed for histology and the other core was processed for mRNA. When only one core could be obtained priority was given to mRNA.

Renal biopsies were processed and read centrally. Formalin-fixed, paraffin-embedded sections were processed for histologic stains (hematoxylin and eosin, periodic acid Schiff, trichrome and Weigerts elastic stains). Immunohistochemistry for C4d was done on an automated stainer on paraffin sections stained with a rabbit polyclonal antibody (American Research Products, Inc.). All slides were scanned with a whole slide scanner (Aperio CS) and high-resolution digital images were archived in an image database.

Biopsies were evaluated and scored separately by 2 renal pathologists, without knowledge of the clinical data, using the well known Revised Banff 2007 Classification for Renal Allograft Pathology (6). Where diagnoses were discordant, a meeting was held with a third pathologist for a consensus diagnosis. Scoring was done on the whole slide images for all cases. Scores were entered into a custom Filemaker Pro database that calculated the Banff categories and Chronic Allograft Damage Index (CADI).

Microarray Experiments, Data Analysis and Cross-Validation

The details of micorarray experiments and data analysis are described below. Briefly, total RNA samples from biopsy samples were extracted and were subjected to microarray experiments using the Affymetrix human exon 1.0 ST array. The intensity data at gene level were extracted with RMA algorithm 7 and corrected for the experimental batch effect using the open source ComBat R package 8 after quality assessment. The genes whose expressions correlated with 3- or 12-month CADI were identified by Spearman correlations analysis and then were subjected to overall Gene Ontology enrichment. The GO functions/pathways associated with CADI-correlated genes from correlation analysis were also validated with Gene Set Enrichment Analysis (GSEA) (9).

To identify a minimal gene set to predict future kidney fibrosis, a focus gene set was employed. The gene set was specifically associated with 12 month CADI as determined by 100 time randomization analysis followed by correction for confounding clinical parameters (CIT, Deceased Donor, Donor Age, Anti HLA antibodies, Acute rejection). An optimal gene set with the best prediction AUC score was identified after 5000 iterations of a fitting penalized logistic regression model on the focus geneset. The gene set was cross-validated using a 3-fold cross-validation method with 100-iterations on our data. The gene set was further validated by quantitative Polymerase Chain Reaction (qPCR) on an independent patient cohort, and also by analysis on three independent publicly available datasets from different array platforms (11-13). Microarray expression files are posted on the Gene Expression Omnibus website (GSE).

Statistical Analysis of Clinical Data

Descriptive statistics (means and standard deviations) were used to summarize the baseline characteristics of donors and recipients, and were compared between study groups (high CADI-12 vs low CADI-12, progressors vs non-progressors) using the chi-square test and Fisher's exact test. Univariate comparisons of continuous variables were done using an unpaired T-test (Mann-Whitney test for corresponding non-parametric analysis). Kaplan-Meier curves were plotted for the duration of the study, with graft loss (not censored for death) as outcome. Survival curves of different groups were compared using the Log-rank test and Gehan-Breslow-Wilcoxon tests. $P<0.05$ was considered significant (GraphPad Prism version 5.03, Graphpad inc, La Jolla, Calif.). To determine the predictive factors for having a high CADI (score≥2) at twelve months post-transplant, multiple logistic regression using backwards predictor selection was performed. The predictors assessed were: donor age, donor race, donor gender, donor status, acute rejection before 3 months, recipient race, recipient gender, expanded criteria donor, induction and maintenance immunosuppressive therapy and the presence of anti HLA antibodies. Cold ischemia time and delayed graft function were considered in a subgroup analysis that included deceased donors only. Logistic models using the same predictors were built to assess predictive factors of progression by month 12 in the full transplant population and the deceased donor only population. All analyses were completed using SAS version 9.2 (SAS, Cary, N.C.).

Supplementary Methods

Clinical Data Collection

Donor and recipient data were collected at baseline. Donor information included age, race, gender, HLA genotype, cause of death, and allograft status (i.e. SCD, ECD, or DCD). Recipient data included age, gender, race, cause of ESRD, HLA genotype, PRA, presence and type of anti-HLA antibodies, cross match status, cold ischemia time (CIT), delayed graft function (DGF), immunosuppression regimen, CMV status, HCV and HBV status, dialysis vintage, dialysis modality, transfusion history, pregnancy history, and previous transplants.

Histopathology:

Two tissue cores were taken from each of the 3-month and 1 year protocol renal biopsies of the Genomics of Chronic Allograft Rejection (GoCAR) cohort. One core was processed for histology and the other core was processed for mRNA. When only one core could be obtained priority was given to mRNA at 3-months and to histology at 12-months. Renal biopsies were processed and read centrally. Formalin-fixed, paraffin-embedded sections were processed for histologic stains (hematoxylin and eosin, periodic acid Schiff, trichrome and Weigerts elastic stains). Immunohistochemistry for C4d was done on an automated stainer on paraffin sections stained with a rabbit polyclonal antibody (American Research Products, Inc.). All slides were scanned with a whole slide scanner (Aperio CS) and high-resolution digital images and archived in an image database.

Biopsies were evaluated and scored separately by 2 renal pathologists, without knowledge of the clinical data, using the Revised Banff 2007 Classification for Renal Allograft Pathology 1 (SIS reference). Where diagnoses were discordant, a meeting was held with a third pathologist for a consensus diagnosis. Scoring was done on the whole slide images for all cases. Scores were entered into a custom Filemaker Pro database that calculated the Banff categories and Chronic Allograft Damage Index (CADI). The CADI-score is a composite score that includes six histologic components—vascular intimal sclerosis (cv), tubular atrophy (ct), interstitial fibrosis (ci), interstitial inflammation (i), mesangial matrix increase (mm) and glomerusclerosis (g). Each component is scored between 0 & 3, giving a maximum possible score of 18. CADI-scores in protocol biospies has been validated to directly correlate with outcomes by several authors2-3.

Microarray Experiments

Total RNA was extracted from percutaneous allograft biopsy samples obtained at 3 month after transplantation using All prep kit (QIAGEN-ALLprep kit, Valencia, Calif. USA) and was stabilized with RNA-later (Qiagen, Inc). RNA quality was assessed using Bioanalyzer 2100 (Agilent Technologies). Samples with an RNA Integrity Number greater than eight were used in subsequent microarray experiments. Affymetrix mouse exon 1.0 ST arrays were used following standard protocol provided by the manufacturer (Affymetrix Inc.). In brief, ENCORE amplification and labeling kit (NuGen, San Carlos, Calif.) was applied to the first batch of samples starting with approximately 100 ng of total RNA to generate biotin-labeled RNA fragments for hybridization to the chip. For samples with a low RNA concentration, the Nugen Ovation PICO amplification kit (NuGen, San Carlos, Calif.) was applied. The chips were scanned using GeneChip Scanner 7G (Affymetrix Inc.).

Microarray Data Processing

The intensity data of microrray experiments at the gene level were extracted and summarized with the RMA algorithm4. Data quality was assessed using the Affymetrix Expression Console (Affymetrix Inc). The Affymetrix control probesets and probesets with low intensity across all samples were excluded from downstream analysis. Batch effects were adjusted using the ComBat R package5.

Bioinformatic Analyses

The workflow of bioinformatic analysis was performed with statistical R packages. The goal of analyses was to derive a relatively robust set of genes (~10-20) that predicts the development of chronic allograft nephropathy.

Identification of the Allograft Transcriptional Signature:

Spearman correlation analyses were performed on the 3-month allograft gene expression data for 3-month allograft CADI score (CADI-3) as well as 12-month CADI score (CADI-12). The correlation coefficient and the p-value for the relationship between the level of expression and CADI score were calculated for each gene. The slope of gene expression against the CADI score was also computed using a linear regression model. Genes with a p value of <0.05 were selected. Two lists of genes with p<0.05 were generated corresponding to either the 3 month or 12 month CADI scores. Annotated functional and molecular mechanisms of these two lists of genes were determined by Gene Ontology (GO) enrichment analysis based on Fisher-exact test. Alternatively, the gene expression dataset was analyzed to determine biological functions that are enriched in biopsies with higher CADI scores. To accomplish this, we applied Gene Set Enrichment Analysis (GSEA) (6-7) to the entire microarray dataset and determined gene functions that are enriched in samples with a high CADI score (CADI≥2) versus those with a low CADI score (CADI<2). Top GO terms associated with both the high and low CADI groups were determined, and compared to the results of GO enrichment analysis derived from the analyses of correlation between gene expression level and CADI score described above.

Prediction Analysis:

To derive a more significant and focused gene set from the large list of genes that have statistically significant association with CADI scores, the gene list was filtered by applying various statistical prediction models. First, the whole cohort of patients was randomly assigned to 2 groups in a 1:1 ratio. Spearman correlation analysis was applied to determine the genes with expressions levels that correlated with the severity of CADI score at 3 and 12 months. The 1:1 randomization was repeated 100 times and correlation analysis of gene expression with CADI score at 3 and 12 month was performed for each of the 100 iterations. Genes that occurred more than twice in the 100 iterations of randomization with a correlation at a P<0.05 with CADI in both groups were considered as a focused gene set from which a minimal prediction set was identified for predicting kidney fibrosis. Genes that were exclusive to the CADI-12 focus gene set (i.e. genes not shared with the CADI-3 focus gene set) were derived and further filtered by correction for clinical confounders (donor age, living vs deceased donor, donor gender and race, CIT min, induction therapy, anti HLA class I, and II antibodies) using multiple linear regression analysis, as well as exclusion of genes with a low median log 2 intensity of less than 5. Finally, iterative logistic model fitting (5000 iterations) was performed in order to identify an optimal and minimal gene set for prediction of future kidney fibrosis. Initially, 20 genes were randomly selected from the filtered CADI-m12 focus gene set. The expression data of the 20-gene group was fitted into the penalized logistic regression model for prediction of high (CADI≥2) and low (CADI<2) CADI. The genes with significant association with high/low CADI (p<0.05) were identified from the regression model for each of the 20-gene group. The steps above were repeated 5000 times. Statistically significant genes (P<0.05) were identified from each iterative operation. The occurrence of significant genes from the 5000 iterations was calculated. Finally, the top 40 genes ranked by the number of occurrences were applied back to the penalized logistic regression model for high vs. low CADI prediction. Statistically significant genes (P<0.05) using this model were considered the final optimal gene set. The AUC score and sensitivity and specificity were calculated from logistic regression model using the final optimal gene set. The receiver operating characteristic curves of the final optimal gene set was compared to randomly selected gene sets of equal size for predicting high vs. low CADI to demonstrate that the final optimal geneset gave the best prediction. In addition, 10000 randomly selected gene sets were selected and AUCs of these gene sets were calculated and compared to the AUC of the final optimal gene set.

The final optimal gene set was cross-validated using a 3-fold cross-validation method. Briefly, the patients were randomly divided into 3 groups of equal size and equal number of high and low CADI patients and the data for any two groups were used as the training set with the third as the prediction set. The penalized logistic regression model that was built on the training set was applied on the prediction set to predict the outcome and the true and false positive rates. Prediction accuracy was calculated from the prediction data set and then averaged from three possible permutations. The steps were repeated over 100 times. The overall true or false positive rates and prediction accuracy were computed. The distribution of AUCs on the testing set based on the model derived using the training set for 100 iterations was plotted. To further assess the confidence of prediction, the group labels were randomly assigned to the patients and AUC were calculated on the group-label permuted data. The steps above were repeated 10000 times and the proportion of AUCs from 10000 iterations were higher than original AUC were calculated.

Prediction of high/low CADI at a different CADI-12 thresholds (high CADI-12≥3 or high CADI-12≥4) was also performed to assess the robustness of 13 geneset prediction. To investigate whether prediction by the gene set is superior to prediction by clinical variables, the multivariate logistic regression was performed for prediction of high/low CADI-12 by including the following demographic/clinical variables: CADI-3, Donor_Age, Deceased_donor, ECD_kidney, DGF, Gender, Race, CIT_min, Induction_Therapy, Anti_HLA_Ab_Class_I, Anti_HLA_Ab_Class_II, Tacrolimus and CYA. After step-wise selection, the variables that remained significant were used in final model. The AUC for the ROC curve of the final model was then calculated and compared to CADI-12 prediction with the geneset. Lastly to check if the inflammation was the driver of 13 gene set, the prediction accuracy of acute rejection was evaluated at 12 month in 101 patients and high/low CADI-12 for the patients without acute rejection.

To test if the gene set could predict early graft loss post-transplant for the original 155 patients after exclusion of the 4 patients who died with a functioning graft, a logistic regression prediction model was firstly applied with the gene set among only those patients who either had graft loss within 3 yr or had been followed-up for at least three years without graft loss and calculated the AUC. Secondly, survival analysis on all 155 patients was performed to examine if the gene set is associated with graft loss: Principle Components Analysis (PCA) on expression data for the 13 genes was initially performed and the top 10 principle components (PC) were applied to Cox proportional hazard model of time to graft loss. The principle components (PC) that were significantly associated with graft loss were selected (p<0.05) and the linear combination of eigenvalues of significant components multiplied by the coefficiencies of corresponding PCs from Cox model was used as the gene set risk score (GR-score). The demographic and clinical variables, including CADI-3, delayed graft function, acute rejection at 3 month or prior, antibodies to HLA1 or HLA2, donor race, donor age, recipient race, recipient age, donor status (living/deceased), and induction therapy, alone or in conjunction with the gene set risk scores were fitted in Cox proportional hazard model of time to graft loss to investigator if any of the demographic or clinical variables are associated with graft loss. The patients were then stratified into two populations based on gene set risk score (GR-score) for Kaplan-meier survival analysis. Finally the time-dependent ROC for graft loss prediction within 2 or 3 yrs post-transplant was plotted and the AUCs calculated.

Validation of Gene Set:

The final optimal gene set was also validated on two independent public datasets. Both public datasets were on the Affymetrix GeneChip platform HU430plus2 (GSE213748, GSE259029). The raw data of these public datasets were processed in Affymetrix Expression Console similar to what is described above for the claimed data set. The expression data for each of the genes in the final optimal gene set was extracted. Predictions of clinical data (graft loss post biopsy at any time for GSE21374, and progressor/non-progressor based on CADI score for GSE25902) was performed using the penalized logistic regression model. AUC scores for each of these 2 data sets were calculated from the ROC curves for prediction specificity over sensitivity. Time to graft loss analysis on data set 1 was also performed (GSE21374) using the same approach as that for GOCAR dataset.

The optimal gene set was also applied to predict the progressors and non-progressors using the same approach described above. Patients who had CADI-3≤3 and demonstrated a ACADI≥2 by 12 month were considered as progressors, and those who had ACADI≤1 were considered non-progressors. Similar assessments were done for those with CADI score at 24 months and also for the patients with CADI-3≤2.

qPCR Example

Total RNA was extracted from allograft biopsy samples of 45 independent cohort patients (18: CADI≥2, and 27:CADI<2) using Allprep kit (QIAGEN-ALLprep kit, Valencia, Calif. USA). cDNA was synthesized using AffinityScript RT kit with oligo dt primers (Agilent Inc. Santa Clara, Calif.). TaqMan qPCR assays for the 13 geneset, 3 house-keeping genes (ACTB, GAPDH and RPLP0) and 18s were purchased from ABI Life Technology (Grand Island, N.Y.). qPCR experiments were performed on cDNA using TAQMAN universal mix and PCR reaction was monitored and acquired using an ABI7900HT system. Samples were measured in triplicates. CT values for the prediction geneset as well as the 3 housing genes were generated. The $\Delta CT$ value of each gene was calculated by subtracting the average CT value for the house-keeping genes from the CT value of each gene and penalized logistic regression fitting model was then applied on $\Delta CT$ values for prediction of the high and low CADI in 45 patients and AUC score was then calculated as described above.

Example 1: Patient Population and Graft Outcome 588 patients were enrolled in the cohort; 204 patients were included in the current study based on inclusion criteria. When quantified using CADI scores, 60% of 12-month biopsies had a CADI of 0-1, 23% of 2-4, and 17% more than 4. As expected, CADI-12 negatively correlated with 12-month eGFR (r=0.35; p=0.0004), and CADI-12≥2 correlated with 3-year graft survival (log rank p=0.007); High CADI-12 was defined as ≥2 based on association with graft survival 5 10. Table 1 summarizes patient demographics based on CADI. In multivariate regression clinical factors significantly associated with high CADI-12 were donor age, recipient).

Microarray was performed on 159 m3_Bx, 101 of which had a corresponding 12-month protocol biopsy. Reasons for lack of 12-month biopsy included graft loss (n=8), death (n=1), lost-to-follow up (n=9), contraindication/inability to obtain biopsy (n=40). There was no difference in clinical variables between 159 microarray patients and the 101 with one-year biopsies (Table 1). 86 patients had a second m3 biopsy core available for pathology, 55% had CADI 0-1, 33% 2-3, and 12% CADI>3. Subclinical acute rejection was diagnosed in 20/86 (23.5%) m3_Bx [13-borderline, 3-IA, 1-IB, 3-IIA], while 52% were reported as normal.

Example 2: Intragraft Molecular Phenotype is Time Dependent

Gene expression profiles from m3_Bx were analyzed by correlation analysis and Gene Set Enrichment Analysis (GSEA) to understand molecular mechanisms of IF/TA (n=159). 1,316 genes were identified that significantly correlated with CADI-3 (806 positively and 510 negatively) and 1,056 genes with CADI-12 (852 positively and 204 negatively) at a cutoff unadjusted p<0.05. Only 176 genes (13.2%) correlated with both CADI-3 and CADI-12. Gene Ontology enrichment indicated that the transcripts specifically associated with CADI-3 alone were related to alloimmunity, including T-cell activation; while genes involved in programmed cell death/apoptosis and cell adhesion were associated with CADI-12 alone. Biological functions were further confirmed by GSEA method in which gene expression data in GO category were compared between patients with high (≥2) and low (<2) CADI at 3- or 12-months.

Example 3: 3-Month Transcriptome Identifies Kidneys at Risk for Chronic Allograft Damage The transcriptome obtained from m3_Bx was analyzed to identify a minimal gene set predictive of CADI-12 (Supplementary methods). Initially a 169 gene set that correlated specifically with CADI-12 but not CADI-3 was identified. These 169 genes were reduced to a set of 85 genes after excluding genes with a low intensity and adjustment for clinical parameters (Table 4). Iterative applications of penalized logistic regression fittings on expression data for these 85 genes identified an optimal 13 gene set that differentiated high CADI-12 from low CADI-12 with an area under the curve (AUC) of 1 (Table 2). This was higher than AUC's for randomly selected 13 gene sets from the initial 85 genes (mean AUC 0.87±0.025). The gene set was subjected to a 3-fold cross-validation method with random assignment to training and test sets (100 times). The average sensitivity, specificity and prediction accuracy for the test sets were 95% 82%, 86%, respectively. The average AUC for the 100 test sets [0.947 (95% CI: 0.942-0.952)] was higher than any AUC that was obtained from the prediction on randomly assigned high and low CADI patient groups with 10000 iterations. The AUCs obtained for CADI-12 at different cutoffs including CADI-12≥3 or ≥4 were 0.986 & 0.963 respectively, confirming the robustness of the gene set of the present invention. Prediction by the gene set was superior to clinico-pathologic variables (AUC=0.783), and combining clinical parameters predictive of high CADI-12 did not enhance the performance of the gene set. Importantly the gene set also accurately predicted fibrosis based on Banff score (Ci+Ct) (AUC=0.092). Subclinical rejection was present in twenty m3_Bx and, was associated with a high CADI-12 (p=0.0003) and BANFF score (Ci+Ct) (p=0.002). Excluding m3_Bx with rejection or i+t>2, did not alter the prediction of high CADI-12 by the gene set disclosed herein (AUC=1), while the 13 genes poorly predicted ACR (AUC=0.743). This taken in conjunction with the ability to predict Ci+Ct demonstrate that inflammation was not the predominant driver for its derivation. Lastly, when validated by qPCR on an independent GoCAR cohort with similar demographics as the training set (Table S4), the gene set accurately differentiated high vs. low CADI-12 (AUC=0.866).

Example 4: Transcriptome Predicts Progression of Chronic Allograft Damage

Next, the gene set was applied to categorize m3_Bx with minimal or no fibrosis into those that would or would not develop progressive fibrosis. From the original 101 patients, those allografts with a CADI-3≤3 (n=68) were identified and two groups were characterized based on change in CADI from 3 to 12 months: (1) progressors (n=1) with ΔCADI≥2; and (2) non-progressors (n=51) with ΔCADI≤1 (Table 1). Table 5 compares 3- and 12-month biopsy pathology scores in progressors vs. non-progressors. Progressors had a higher CADI at 3 months predominantly driven by the ci score; however CADI-3 alone could not be used to differentiate progressor from non-progressor. Clinical parameters were also poor predictors of progression (AUC=0.642). The disclosed gene set accurately identified CADI-progressors from non-progressors (ΔCADI≥2) at both 12-months (AUC 0.984) and 24-month (AUC 0.859). Furthermore it predicted CADI-progression by 12- and 24-months equally well when pristine allografts with CADI-3≤2 were analyzed (AUC=1 and 0.84, respectively). These findings are of clinical importance since progressors had poorer graft survival than non-progressors at 36-months follow-up (Gehan-Breslow-Wilcoxon p=0.01; Log-rank p=0.06)

Example 5: Transcriptome Signature Predicts Early Allograft Loss

Cox-models were next generated with the gene set of the present invention and clinical variables to predict death-censored graft loss on the disclosed cohort (graft loss n=11). Three principle components (P4, P6 and P7) of expression data of 13-genes were significantly associated graft loss in the Cox proportional hazard model (p<0.05)(Table S5) and used to derive the "gene set risk score" (GR-score) (Graft loss HR 2.719, 95% CI 1.60-4.63). Patients were stratified into two groups of equal size based on this GR-score and higher scores were significantly associated with graft loss (Log-rank p<0.002). Using the GR-score, AUC's for time-dependent graft loss within 2- & 3-yrs post-transplant were 0.863 and 0.849, respectively. Among clinical variables, only delayed graft function was significantly associated with graft loss (Table 6). However combination of gene set with delayed graft function did not improve prediction.

Example 6: Validation of the Predictive Gene Set

To confirm the utility of the 13 gene set in diverse settings, two independent, publically available data sets were analyzed using the endpoints of graft loss and CADI as indicators of chronic allograft injury (Table 9). The gene set accurately predicted the relative endpoint for each of the data sets, outperforming the AUC reported by the original studies. Survival analysis for data set-1 using the gene set of the present invention showed significant differences between stratified high- and low-risk groups for graft loss (p=2.1e-9); AUC's for graft loss within 1- and 2-yrs after biopsy were 0.865 and 0.807, respectively. These data demonstrate that this 13 gene set can be applied across populations for the prediction of diverse yet clinically important outcomes including allograft survival.

Example 7: 13 Gene Signature Set Pursuant to Present Invention

KLHL13, KAAG1, MET, SPRY4, SERINC5, CHCHD10, FJX1, WNT9A, RNF149, ST5, TGIF1, RXRA, ASB15. The art recognized names of these genes is shown in Table 3.

TABLE 1

Demographic and clinical characteristics (High- and Low-CADI-12; CADI-Progressors and Non-Progressors

| Characteristics | 159 patients in microarray Mean ± SD (%) | 101 patients with CADI-12 Mean± (%) | P-value* | High CADI n = 40 Mean ± SD (%) | Low CADI n = 61 Mean ± SD (%) | P-value# | 17 Progressors ΔCADI ≥ 2 Mean ± SD (%) | 51 Non-Progressors ΔCADI < 2 Mean ± SD (%) | P-value# |
|---|---|---|---|---|---|---|---|---|---|
| Recipient age | 48.84 ± 13.27 | 46.90 ± 12.38 | 0.24 | 48.17 ± 13.32 | 47.36 ± 13.00 | 0.96 | 48.98 ± 14.34 | 46.83 ± 12.79 | 0.56 |
| Recipient gender - Female | 47 (29.35) | 26 (25.70) | 0.57 | 16 (40.00) | 10 (16.67) | 0.03 | 9 (52.94) | 10 (19.61) | 0.01 |
| Recipient race | | | | | | | | | |
| White | 92 (57.86) | 66 (65.35) | 0.33 | 23 (57.5) | 43 (70.50) | 0.99 | 8 (47.05) | 39 (76.47) | .028 |
| African-American | 37 (23.27) | 15 (14.85) | | 6 (15.0) | 9 (14.76) | | 4 (23.52) | 5 (9.80) | |
| Hispanic | 14 (8.82) | 7 (6.93) | | 4 (10) | 3 (4.91) | | 2 (11.76) | 2 (3.92) | |
| Other/Unreported | 16 (10.12) | 13 (12.87) | | 7 (17.5) | 6 (9.83) | | 3 (17.65) | 5 (9.80) | |
| Recipient ESRD diagnosis | | | | | | | | | |
| Diabetic nephropathy | 57 (35.85) | 33 (32.67) | 0.52 | 12 (30.0) | 21 (34.42) | 0.63 | 4 (23.52) | 17 (33.33) | 0.90 |
| Hypertension | 24 (15.09) | 17 (16.83) | | 7. (17.5) | 10 (16.39) | | 4 (23.52) | 8 (15.69) | |
| Glomerulonephritis | 28 (17.61) | 22 (21.78) | | 7 (17.5) | 15 (24.59) | | 3 (17.65) | 10 (19.61 | |
| Polycystic Kidney | 14 (8.82) | 13 (12.87 | | 5 (12.5) | 8 (13.11) | | 3 (17.65) | 7 (13.72) | |
| Other | 36 (22.64) | 16 (15.84) | | 9 (22.5) | 7 (13.11) | | 3 (17.65) | 9 (17.64) | |
| Prior renal transplant, n (%) | 4 (2.51) | 2 (1.98) | 1.00 | 2 (5) | 0 (0) | 0.15 | 1 (5.88) | 1 (1-9) | 0.45 |
| Donor age | 41.13 ± 16.80 | 40.73 ± 16.80 | 0.87 | 47.08 ± 17.91 | 36.5714.75 | 0.008 | 43.94 ± 17.80 | 37.47 ± 17.01 | 0.18 |
| Donor gender - Female | 77 (48.13) | 46 (45.54) | 0.70 | 17 (42.50) | 29 (48.33) | 0.69 | 5 (29.41) | 24 (47.06) | 0.17 |
| Donor race | | | | | | | | | |
| Caucasian | 121 (75.6) | 80 (79.21) | 0.64 | 31 (77.5) | 49 (80.32) | 1.00 | 13 (76.47) | 42 (82.35) | 0.99 |
| African-American | 17 (10.63) | 8 (7.92) | | 4 (10.0) | 4 (6.55) | | 2 (11.76) | 3 (5.88) | |
| Hispanic | 12 (7.54) | 5 (4.95) | | 1 (2.5) | 4 (6.55) | | 1 (5.88) | 3 (5.88) | |
| Other/Unreported | 9 (5.66) | 8 (7.92) | | 4 (10.0) | 7 (11.47) | | 1 (5.88) | 3 (5.88) | |
| Donor Status Deceased/Living | 94/65 | 58/43 | 0.79 | 25/15 | 33/28 | 0.42 | 10/7 | 28/23 | 1.00 |
| 3-month Serum Creatinine | 1.39 ± 0.43 | 1.32 ± 0.38 | 0.26 | 1.321 ± 0.2947 | 1.325 ± 0.4326 | 0.96 | 1.36 ± .030 | 1.32 ± 0.30 | 0.66 |
| 3-month CADI-Mean ± SD | 1.63 ± 1.76 | 1.66 ± 1.79 | | 2.57 ± 2.08 | 1.06 ± 1.28 | <0.001 | 1.53 ± 1.18 | 0.86 ± 0.98 | 0.66 |
| Median (IQR) | 1 (3-0) | 1 (3-0) | | 2 (3-1) | 1 (2-0) | | 1.5 (3-0.25) | 1 (1.5-0) | |
| Cold Ischemica time (hrs)* | 14.64 ± 6.78 | 13.84 ± 6.74 | 0.46 | 15.63 ± 7.63 | 12.39 ± 5.11 | 0.05 | 16.32 ± 10.65 | 12.78 ± 5.147 | 0.17 |
| h/o Delayed graft function* | 21 (13.21) | 9 (8.91) | 0.32 | 7 (28.0) | 2 (6.06) | 0.009 | 4 (23.52) | 4 (7.84) | 0.17 |
| Anti-HLA antibodies** | 35 (23.17) | 25 (26.59) | 0.53 | 11 (28.20) | 14 (25.45) | 0.63 | 3 (33.33) | 8 (15.68) | 1.00 |
| DSA positive | 11 (7.28 | 7 (7.44) | | 3 (7.69) | 4 (7.27) | | 3 (16.66) | 4 (7.84) | |
| Class-I | 8 (5.29) | 6 (6.38) | | 3 (7.69) | 3 (5.45) | | 3 (16.66) | 2 (3.92) | |
| Class-II | 6 (3.97) | 2 (2.12) | | 0 (0.0) | 2 (3.64) | | 0 (0.0) | 3 (5.88) | |
| Non-DSA positive | 25 (16.55) | 20 (21.27) | | 8 (20.51) | 12 (21.81) | | 0 (0.0) | 6 (11.76) | |

TABLE 1-continued

Demographic and clinical characteristics (High- and Low-CADI-12; CADI-Progressors and Non-Progressors

| Charac-teristics | 159 patients in microarray Mean ± SD (%) | 101 patients with CADI-12 Mean± (%) | P-value* | High CADI n = 40 Mean ± SD (%) | Low CADI n = 61 Mean ± SD (%) | P-value# | 17 Progressors ΔCADI ≥ 2 Mean ± SD (%) | 51 Non-Progressors ΔCADI < 2 Mean ± SD (%) | P-value# |
|---|---|---|---|---|---|---|---|---|---|
| Class-I | 25 (16.55) | 20 (21.27) | | 8 (20.51) | 12 (21.81) | | 0 (0.0) | 6 (11.76) | |
| Class-II | 13 (8.61) | 7 (7.44) | | 3 (7.69) | 4 (7.27) | | 0 (0.0) | 4 (7.84) | |
| Induction therapy | | | | | | | | | |
| Thymo-globulin | 49 (30.81) | 26 (25.74) | 0.67 | 12 (30.0) | 14 (22.95) | 0.47 | 5 (29.41) | 9 (17.65) | 0.24 |
| Anti-CD25 therapy | 52 (32.70) | 38 (37.63) | | 17 (42.5) | 21 (34.42) | | 9 (52.94) | 19 (37.25) | |
| Campath | 9 (5.66) | 8 (7.92) | | 2 (5.0) | 6 (9.83) | | 1 (5.88) | 6 (11.76) | |
| None | 49 (30.81) | 29 (28.71) | | 9 (22.5) | 20 (32.78) | | 2 (16.67) | 17 (33.33) | |
| 12-month Maintenance immuno-suppression | | | | | | | | | |
| MMF, CNI, steroids | 139 (87.42) | 90 (89.11) | 0.72 | 37 (92.5) | 53 (86.89) | 0.84 | 16 (94.12) | 44 (84.61) | 0.75 |
| MMF, CNI | 12 (7.55) | 8 (7.92) | | 2 (5.0) | 6 (9.84) | | 1 (5.88) | 7 (13.46) | |
| Others | 8 (5.03) | 3 (2.97) | | 1 (2.5) | 2 (3.27) | | 0 (0.0) | 1 (1.92 | |
| 1-year acute rejection | 22 (13.84) | 22 (21.78) | NA | 18 (45.00) | 4 (6.56) | <0.01 | 7 (41.18) | 5 (9.80) | <0.01 |

Legend:
CADI—chronic allograft damage index at 12-months; MFI—mean fluorescence Intensity; MMF—mycophenolate mofetil; CNI—calcineurin inhibitors; DSA—donor specific antibody;
*Deceased donors only; **94/101 patients had HLA antibodies measured.
P value determined by Mann-Whitney test (non-parametric comparisons) or unpaired T-test.

TABLE 2

Multivariate analysis-Clinical covariates predictive of CADI-score at 12-months ≥2 Odds Ratio Estimates

| Effect | Point Estimate | 95% Wald Confidence Limits | | P-value# |
|---|---|---|---|---|
| Donor Age | 1.062 | 1.025 | 1.100 | 0.0007 |
| Donor status (DD*vs LD**) | 4.292 | 1.311 | 14.054 | 0.0161 |
| ACR (before 3-mths) (Yes vs No) | 3.014 | 1.023 | 8.876 | 0.0453 |
| Recipient race (non-caucasian vs Caucasian) | 1.709 | 0.591 | 4.947 | 0.3227 |
| Recipient_Gender (Female vs Male) | 6.653 | 1.900 | 23.294 | 0.0030 |
| Induction_Therapy*** | | | | |
| Lymphocyte depleting | 1.445 | 0.408 | 5.111 | 0.8515 |
| Lymphocyte non-depleting | 2.550 | 0.660 | 9.855 | 0.1915 |
| antiHLA antibodies (No vs Yes) | 0.358 | 0.092 | 1.399 | 0.1397 |

P-value-Wald Chi-square, *DD-Deceased donor, **LD-Living donor
***Induction therapy category compares Lymphocyte depleting and Lymphocyte non-depleting induction to No induction therapy

TABLE 3

13 Gene Prediction Set

| ProbeID | Symbol | Gene Description | Cytoband | mRNA Accession | CADI Corr | Pvalue |
|---|---|---|---|---|---|---|
| 3326826 | FJX1 | four jointed box 1 (*Drosophila*) | 11p13 | NM_01433 | 0.384142 | 7.31E−05 |
| 4019160 | KLHL13 | kelch-like 13 (*Drosophila*) | Xq23-q24 | NM_001168302 | 0.380008 | 8.87E−05 |
| 3954887 | CHCHD10 | coiled-coil-helix-coiled-coil-helix domain containing 10 | 22q11.23 | NM_213720 | 0.338868 | 0.000528 |
| 2864449 | SERINC5 | serine incorporator 5 | 5q14.1 | NM_001174072 | 0.330535 | 0.000736 |
| 3020343 | MET | met proto-oncogene (hepatocyte growth factor receptor) | 7131 | NM_001127500 | 0.325015 | 0.000912 |
| 2567583 | RNF149 | ring finger protein 149 | 2q11.2 | NM_173647 | 0.304022 | 0.001996 |
| 2879105 | SPRY4 | sprouty homolog 4 (*Drosophila*) | 5431.3 | NM_030964 | 0.303968 | 0.002 |
| 2898441 | KAAG1 | kidney associated antigen 1 | 6p22.1 | NM_81337 | 0.264688 | 0.007476 |
| 3776504 | TGIF1 | TGFB-induced factor homeobox 1 | 18p11.3 | NM_170695 | 0.248915 | 0.012071 |
| 2459352 | WNT9A | wingless-type MMTV integration site family, member 9A | 1q42 | NM_003395 | 0.237215 | 0.016917 |

TABLE 3-continued

13 Gene Prediction Set

| ProbeID | Symbol | Gene Description | Cytoband | mRNA Accession | CADI Corr | Pvalue |
|---|---|---|---|---|---|---|
| 3361971 | ST5 | suppression of tumorigenicity 5 | 11p15 | NM_005418 | 0.231432 | 0.019879 |
| 3021696 | ASB15 | ankyrin repeat and SOCS box-containing 15 | 7q31.31 | NM_080928 | −0.2548 | 0.010128 |
| 3193339 | RXRA | retinoid X receptor, alpha | 9434.3 | NM_002957 | −0.30533 | 0.001904 |

TABLE 4

The 85 focus geneset

| Probe ID | Gene Symbol | Gene Description | Cytoband | mRNA Acc | CADI Corr | Pvalue | Slope |
|---|---|---|---|---|---|---|---|
| 2761842 | PROM1 | prominin 1 | 4p15.32 | NM_00114 | 0.358 | 0.000 | 0.138 |
| 3040518 | MACC1 | metastasis associated in colon cancer 1 | 7p21.1 | NM_18276 | 0.407 | 0.000 | 0.109 |
| 2583465 | ITGB6 | integrin, beta 6 | 2q24.2 | NM_00088 | 0.340 | 0.000 | 0.102 |
| 2974413 | MOXD1 | monooxygenase, DBH-like 1 | 6q23.2 | NM_01152 | 0.316 | 0.001 | 0.100 |
| 2868265 | LIX1 | Lix1 homolog (chicken) | 5q15 | NM_15323 | 0.329 | 0.001 | 0.098 |
| 2669979 | CX3CR1 | chemokine (C—X3—C) receptor 1 | 3p21-3p23 | NM_00117 | 0.278 | 0.005 | 0.095 |
| 2721959 | SLC34A2 | solute carrier family 34 (sodium phosphate), member 2 | 4p15.3- | NM_00117 | 0.354 | 0.000 | 0.091 |
| 3167110 | ANZA2P2 | annexin A2 pseudogene 2 | 9p13 | NM_00357 | 0.335 | 0.001 | 0.084 |
| 3596147 | GCNT3 | glucosaminyl (N-acetyl) transferase 3, mucin type | 15q21.3 | NM_00475 | 0.369 | 0.000 | 0.083 |
| 3129065 | CLU | clusterin | 8p21-p12 | NM_00183 | 0.347 | 0.000 | 0.080 |
| 2315918 | ATAD3C | ATPase family, AAA domain containing 2C | 1p36.33 | NM_00103 | 0.268 | 0.007 | 0.080 |
| 3020192 | TES | testis derived transcript (3 LIM domains) | 7q31.2 | NM_01564 | 0.343 | 0.000 | 0.080 |
| 4019160 | KLHL13 | kelch-like 13 (Drosophila) | Xq23-q24 | NM_00116 | 0.380 | 0.000 | 0.072 |
| 2602770 | DNER | delta/notch-like EGF repeat containing | 2q36.3 | NM_13907 | 0.327 | 0.001 | 0.066 |
| 3471753 | C12orf47 | chromosome 12 open reading frame 47 | 12q24.12 | NR_015404 | 0.214 | 0.032 | 0.066 |
| 2898441 | KAAG1 | kidney associated antigen 1 | 6p22.1 | NM_18133 | 0.265 | 0.007 | 0.062 |
| 2486927 | ARHGAP25 | Rho GTPase activating protein 25 | 2p13.3 | NM_01488 | 0.300 | 0.002 | 0.062 |
| 3415320 | KRT7 | keratin 7 | 12q12-q13 | NM_00555 | 0.251 | 0.011 | 0.061 |
| 2787902 | GYPE | glycophorin E (MNS blood group) | 4q31.1 | NM_19868 | 0.281 | 0.004 | 0.059 |
| 3020343 | MET | met proto-oncogene (hepatocyte growth factor receptor) | 7q31 | NM_00112 | 0.325 | 0.001 | 0.057 |
| 2414958 | TACSTD2 | tumor-associated calcium signal transducer 2 | 1p32-p31 | NM_00235 | 0.240 | 0.015 | 0.057 |
| 3405587 | GPRC5A | G protein-coupled receptor, family C, group 5, member A | 12p13-p12 | NM_00397 | 0.277 | 0.005 | 0.057 |
| 2344888 | CYR61 | cysteine-rich, angiogenic inducer, 61 | 1p31-922 | NM_00155 | 0.349 | 0.000 | 0.055 |
| 3960061 | RAC1 | ras-related C3 botulinum toxin substrate 2 (rho family, small GTP binding protein | 22q13.1 | NM_00287 | 0.235 | 0.018 | 0.055 |
| 2672140 | LTF | lactotransferrin | 3p21.31 | NM_00234 | 0.287 | 0.004 | 0.055 |
| 2879105 | SPRY4 | sprout homolog 4 (Drosophila) | 5q31.3 | NM_03096 | 0.304 | 0.002 | 0.053 |
| 2864449 | SERINC5 | serine incorporator 5 | 5q14.1 | NM_00117 | 0.331 | 0.001 | 0.049 |
| 3168938 | POLR1E | polymerase (RNA) 1 polypeptide E, 53kDa | 9q13.2 | NM_02249 | 0.250 | 0.012 | 0.047 |
| 2356142 | LIX1L | Lix1 homolog (mous)-like | 1q21.1 | NM_15371 | 0.257 | 0.009 | 0.047 |
| 3464860 | DUSP6 | dual specificity phosphate 6 | 12q22-q23 | NM_00194 | 0.382 | 0.000 | 0.047 |
| 3108489 | LAPTM4B | lysosomal protein transmembrane 4 beta | 8q22.1 | NM_01840 | 0.316 | 0.001 | 0.047 |
| 2374982 | RNPEP | arginyl aminopeptidase (aminopeptidase B) | 1q32 | NM_02021 | 0.286 | 0.004 | 0.044 |
| 3796620 | DLGAP1 | discs, large (Drosophila) homolog-associated protein 1 | 18p11.3 | NM_00474 | 0.363 | 0.000 | 0.044 |
| 3662041 | OGFOD1 | 2-oxoglutarate and iron-dependent oxygenase domain-containing protein 1 | 16q12.2 | NM_01823 | 0.284 | 0.004 | 0.043 |
| 2323899 | UBXN10 | UBX domain protein 10 | 1p36.12 | NM_15237 | 0.226 | 0.023 | 0.043 |
| 3332913 | TMEM216 | transmembrane protein 216 | 11q13.1 | NM_01649 | 0.244 | 0.014 | 0.043 |
| 3954887 | CHCHD10 | coiled-coli-helix-coiled-coli-helix domain containing 10 | 22q11.23 | NM_21372 | 0.339 | 0.001 | 0.043 |
| 3850445 | CDKN2D | cyclin-dependent kinase inhibitor 2D (p19, inhibits CDK4) | 19q13 | NM_00180 | 0.263 | 0.008 | 0.042 |
| 3232349 | PFKP | phosphofructokinase, platelet | 10p915.3 | NM_00262 | 0.247 | 0.013 | 0.041 |
| 2881187 | CSF1R | colony stimulating factor 1 receptor | 5q33-q35 | NM_00521 | 0.240 | 0.016 | 0.041 |
| 3820443 | ICAM1 | intercellular adhesion molecule 1 | 19p13.3 | NM_00020 | 0.245 | 0.013 | 0.040 |
| 3326826 | FJX1 | four jointed box 1 (Drosophila) | 11p13 | NM_01434 | 0.384 | 0.000 | 0.040 |
| 2825629 | TNFAIP8 | tumor necrosis factor, alpha-induced protein 8 | 5q23.1 | NM_01435 | 0.294 | 0.003 | 0.040 |
| 3868998 | NKG7 | natural killer cell group 7 sequence | 19q13.41 | NM_00560 | 0.243 | 0.014 | 0.039 |
| 3726154 | ITGA3 | integrin, alpha 3 (antigen CD49C, alpha 3 subunit of VLA-3 receptor | 17q21.33 | NM_00220 | 0.263 | 0.008 | 0.039 |
| 3024025 | MEST | mesoderm specific transcript homolog (mouse) | 7q32 | NM_00240 | 0.291 | 0.003 | 0.038 |
| 2459352 | WNT9A | wingless-type MMTV integration site family, member 9A | 1q42 | NM_00339 | 0.237 | 0.017 | 0.037 |
| 2872335 | ZNF416 | zinc finger protein 416 | 19q13.4 | NM_01787 | 0.283 | 0.004 | 0.037 |
| 2899437 | BTN2A1 | butyrophilin, subfamily 2, member A1 | 6p22.1 | NM_07847 | 0.255 | 0.010 | 0.037 |

TABLE 4-continued

The 85 focus geneset

| Probe ID | Gene Symbol | Gene Description | Cytoband | mRNA Acc | CADI Corr | Pvalue | Slope |
|---|---|---|---|---|---|---|---|
| 3734648 | SLC16A5 | solute carrier family 16, (monocarboxylic acid transporter) member 5 | 17q25.1 | NM_00469 | 0.279 | 0.005 | 0.037 |
| 3605395 | ADAMTSL3 | ADAMTS-like 3 | 15q25.2 | NM_20751 | 0.320 | 0.001 | 0.036 |
| 2435218 | TDRKH | tudor and KH domains-containing protein | 1q21 | NM_00108 | 0.272 | 0.006 | 0.033 |
| 2876361 | PITX1 | paired-like homeodomain transcription factor 1 | 5q31 | NM_00265 | 0.246 | 0.013 | 0.033 |
| 2621881 | P4HTM | prolyl 4-hydroxylase, transmembrane (endo-plasmic reticulum) | 3p21.31 | NM_17793 | 0.293 | 0.003 | 0.032 |
| 2407985 | HEYL | hair/enhancer-of-split related with YRPW | 1p34.3 | NM_01457 | 0.240 | 0.016 | 0.031 |
| 3270270 | PTPRE | protein tyrosine phosphatase, receptor type, E | 10q26 | NM_00650 | 0.255 | 0.010 | 0.031 |
| 3738471 | RAC3 | ras-related C3 botulinum toxin substrate 3 (rho family, small GTP-binding protein | 17q25.3 | NM_00505 | 0.246 | 0.013 | 0.030 |
| 3028217 | — | — | — | AK303101 | 0.243 | 0.014 | 0.030 |
| 3888383 | SLC9A8 | solute carrier familyl 9 (sodium/hydrogen exchanger), member 8 | 20q13.13 | NM_01526 | 0.299 | 0.002 | 0.030 |
| 2567583 | RNF149 | ring finger protein 149 | 2q11.2 | NM_17634 | 0.304 | 0.002 | 0.030 |
| 3056264 | ABHD11 | abhydrolase domain containing 11 | 7q11.23 | NR_026912 | 0.251 | 0.011 | 0.029 |
| 3261009 | KAZALD1 | Kazal-type serine peptidase inhibitor domain 1 | 10q24.31 | NM_03092 | 0.251 | 0.011 | 0.029 |
| 2369484 | TOR3A | torsin family 3, member A | 1q25.2 | NM_02237 | 0.279 | 0.005 | 0.028 |
| 2931391 | MTHFD1L | mthylenetetrahydrofolate dehydrogenase 1-like, NAPD(+)-dependent) | 6q25.1 | NM_01544 | 0.299 | 0.002 | 0.028 |
| 3361971 | ST5 | suppression of tumorigenicity 5 | 11p15 | NM_00541 | 0.231 | 0.020 | 0.028 |
| 3623717 | FLJ10038 | hypothetical protein FLJ10038 | 15q21.2 | NR_026891 | 0.277 | 0.005 | 0.028 |
| 2361342 | SEMA4A | sema domain, immunoglobulin domain (Ig), transmembrane domain | 1q22 | NM_02236 | 0.229 | 0.021 | 0.026 |
| 3051655 | VOPP1 | vesicular, overpressed in cancer, prosurvival protein 1 | 7p11.2 | NM_03079 | 0.229 | 0.021 | 0.025 |
| 3776504 | TGIF1 | TGFB-induced factor homeobox 1 | 18p11.3 | NM_17069 | 0.249 | 0.012 | 0.025 |
| 2692319 | ADCY5 | adenylate cyclase 5 | 3q13.2-21 | NM_18335 | 0.200 | 0.044 | 0.025 |
| 2933392 | SYNJ2 | synaptojanin 2 | 6q25.3 | NM_00389 | 0.283 | 0.004 | 0.024 |
| 3185593 | BSPRY | B-box and SPRY domain containing | 9q32 | NM_01768 | 0.279 | 0.005 | 0.023 |
| 3865998 | PNMAL1 | PNMA-like 1 | 19q13.32 | NM_01821 | 0.234 | 0.019 | 0.023 |
| 2359885 | SLC27A3 | solute carrier family 27 (fatty acid transporter), member 3 | 1q21.3 | NM_02433 | 0.237 | 0.017 | 0.022 |
| 2714132 | PDE6B | phosphodiesterase 6B, cGMP-specific, rod, beta | 4p16.3 | NM_00028 | 0.272 | 0.006 | 0.022 |
| 3224087 | TTLL11 | tubulin tyrosine ligase-like family, member 11 | 9q33.2 | NM_00113 | 0.248 | 0.012 | 0.021 |
| 3431892 | SH2B3 | SH2B adaptor protein 3 | 12q24 | NM_00547 | 0.307 | 0.002 | 0.018 |
| 3193339 | RXRA | retinoid X receptor, alpha | 9q34.3 | NM_00295 | −0.305 | 0.002 | −0.025 |
| 3645901 | NAT15 | N-acetyltransferase 15 (GCN5-related, putative) | 16p13.3 | NM_02484 | −0.298 | 0.002 | −0.040 |
| 2942578 | CCDC90A | coiled-coil domain containing 90A | 6p24.3-p23 | NM_00103 | 0.268 | 0.007 | −0.044 |
| 3907507 | C20orf165 | chromosome 20 open reading frame 165 | 20q13.12 | NM_08060 | −0.219 | 0.028 | −0.049 |
| 3305801 | SORCS1 | sortilin-related VPS10 domain containing receptor 1 | 10q23-q25 | NM_05291 | −0.272 | 0.006 | −0.060 |
| 3021696 | ASB15 | ankyrin repeat- and SOCS box-containing 15 | 7q31.31 | NM_08092 | −0.255 | 0.010 | −0.102 |
| 3394412 | THY1 | Thy-1 cell surface antigen | 11q22.3 | NM_00628 | −0.239 | 0.016 | −0.112 |
| 3635903 | LOC388152 | hypothetical LOC388152 | 15q25.2 | BC054509 | −0.212 | 0.033 | −0.136 |

TABLE 5

CADI subscore comparisons between prog/non-progressor

| Parameter | 3-month | | | 12-month | | |
|---|---|---|---|---|---|---|
| | Progressors Mean ± SD | Non-Progressors Mean ± SD | *p-value | Progressors Mean ± SD | Non-progressors Mean ± SD | *p-value |
| CADI | 1.53 ± 1.18 | 0.86 ± 0.98 | 0.03 | 5.65 ± 2.47 | 0.96 ± 0.98 | <0.0001 |
| ct-score | 0.56 ± 0.51 | 0.41 ± 0.50 | 0.29 | 1.53 ± 0.87 | 0.52 ± 0.50 | <0.0001 |
| cv-score | 0.0 ± 0.0 | 0.02 ± 0.14 | 0.64 | 0.0 ± 0.0 | 0.0 ± 0.0 | NA |
| ci-score | 0.44 ± 0.63 | 0.10 ± 0.30 | <0.01 | 1.71 ± 1.11 | 0.16 ± 0.37 | <0.0001 |
| i-score | 0.06 ± 0.25 | 0.08 ± 0.34 | 0.98 | 1.71 ± 0.92 | 0.06 ± 0.23 | <0.0001 |
| mm-score | 0.0 ± 0.0 | 0.02 ± 0.14 | 0.61 | 0.25 ± 0.68 | 0.0 ± 0.0 | 0.01 |
| g-score | 0.28 ± 0.73 | 0.16 ± 0.58 | 0.47 | 0.06 ± 0.25 | 0.12 ± 0.52 | 1.00 |

*Mann-Whitney test

TABLE 6

Baseline clinical and demographic characteristics for GoCAR patient cohorts.

| Characteristics: | Microarray patients (n = 101) Mean ± SD (%) | RT-PCR patients (n = 45) Mean ± SD (%) | *P-value |
|---|---|---|---|
| Recipient age | 46.90 ± 12.38 | 46.81 ± 11.52 | 0.69 |
| Recipient race | | | 0.96 |
| Caucasian | 66 (65.35) | 33 (73.33) | |
| African American | 15 (14.85) | 3 (6.67) | |
| Other | 20 (19.80) | 9 (20.0) | |
| Recipient ESRD diagnosis | | | 0.63 |
| Diabetic nephropathy | 33 (32.67) | 10 (22.22) | |
| Hypertension | 17 (16.83) | 6 (13.33) | |
| Glomerulonephritis | 22 (21.78) | 15 (33.33) | |
| Polycystic Kidney | 13 (12.87) | 5 (11.11) | |
| Other | 16 (15.84) | 9 (20.00) | |
| Donor age | 40.73 ± 16.80 | 44.87 ± 14.68 | 0.16 |
| Donor race | | | 0.72 |
| Caucasian | 80 (79.21) | 42 (93.33) | |
| Non-Caucasian | 21 (20.79) | 3 (6.67) | |
| h/o Delayed graft function | 9 (8.91) | 5 (11.11) | 0.54 |
| Anti-HLA antibodies** | 19 (20.21) | 19 (42.22) | <0.01 |
| Class-I | 19 (20.21) | 19 (42.22) | |
| Class-II | 4 (3.90) | 12 (26.67) | |
| 3-month eGFR-creatinine | 62.53 ± 17.90 | 59.27 ± 18.91 | 0.37 |
| 3-month Acute rejection# | 20 (22.7) | 11 (28.94) | 0.36 |
| High/low CADI-12 | 40/61 | 18/27 | 1.00 |
| High CADI-12 | | | 0.34 |
| Mean ± SD | 4.58 ± 2.25 | 4.00 ± 2.09 | |
| Median(IQR) | 4 (3.0-5.0) | 3 (2.75-5.0) | |
| Low CADI-12 | | | 0.96 |
| Mean ± SD | 0.48 ± 0.50 | 0.48 ± 0.51 | |
| Median(IQR) | 0.0 (0.0-1.0) | 0.0 (0.0-1.0) | |

*P-value by Unpaired T-test (or non-parametric) and, Chi-square/Fisher's exact test.
**94/101 & 38/45 patients had HLA antibodies measured.
86/103 & 40/45 patients had 3-month biopsy reported for histology

TABLE 7

Association of 10 principle components of 13 geneset with graft loss in Cox proportional hazard model

| PC | coef | exp(coef) | se(coef) | z | P | |
|---|---|---|---|---|---|---|
| PC1 | −0.396 | 6.73E−01 | 32.66 | −0.0121 | 0.99 | |
| PC2 | −6.845 | 1.06E−03 | 7 | −0.9778 | 0.33 | |
| PC3 | −0.931 | 3.94E−01 | 7.96 | −0.117 | 0.91 | |
| PC4 | −14.933 | 3.27E−07 | 5.03 | −2.9692 | 0.003 | * |
| PC5 | 1.366 | 3.92E+00 | 3.87 | 0.3532 | 0.72 | |
| PC6 | 12.233 | 2.05E+05 | 5.14 | 2.38 | 0.017 | * |
| PC7 | 9.201 | 9.90E+03 | 4.44 | 2.0735 | 0.038 | * |
| PC8 | 0.824 | 2.28E+00 | 3.8 | 0.2166 | 0.83 | |
| PC9 | −2.674 | 6.90E−02 | 5.18 | −0.5159 | 0.61 | |
| PC10 | −2.771 | 6.26E−02 | 4.02 | −0.6889 | 0.49 | |

Likelihood ratio test = 20.7 on 10 df, p = 0.023, n = 155, number of events = 11

TABLE 8

Association of demographic or clinical variables with graft loss in Cox proportional hazard mode

| Variable | Coef | Exp(coef) | SE(coef) | Z | P |
|---|---|---|---|---|---|
| ACR_M3_and_less | 2.5635 | 1.30E+01 | 1.31E+00 | 1.96E+00 | 0.05 |
| Delayed_Graft_Function | 1.8058 | 6.08E+00 | 8.64E−01 | 2.09E+00 | 0.037* |
| M3_CADI | −0.196 | 8.22E−01 | 2.84E−01 | −6.89E−01 | 0.49 |
| Donor_Status (Living vs deceased) | 1.5616 | 4.77E+00 | 1.39E+00 | 1.12E+00 | 0.26 |
| HLA1_n | 19.1431 | 2.06E+08 | 1.78E+04 | 1.08E−03 | 1 |
| HLA1_ndsa | 0.9569 | 2.60E+00 | 2.18E+04 | 4.39E−05 | 1 |
| HLA2_n | 15.5608 | 5.73E+06 | 7.23E+04 | 2.15E−04 | 1 |
| HLA2_ndsa | 34.0887 | 6.38E+14 | 7.34E+04 | 4.64E−04 | 1 |
| Induction_Type_LND | 0.0239 | 1.02E+00 | 1.37E+00 | 1.74E−02 | 0.99 |
| Induction_Type_None | −0.5606 | 5.71E−01 | 1.78E+00 | −3.15E−01 | 0.75 |
| Donor_Race: Black/African American | −0.5692 | 5.66E−01 | 2.15E+00 | −2.65E−01 | 0.79 |
| Donor_Race: Hispanic | −19.7123 | 2.75E−09 | 1.59E+04 | −1.24E−03 | 1 |
| Donor_Race: Pacific Islander | −2.7581 | 6.34E−02 | 1.19E+05 | −2.31E−05 | 1 |
| Donor_Race: White/Caucasian | −0.1417 | 8.68E−01 | 1.78E+00 | −7.98E−02 | 0.94 |
| Race: Black/African American | −0.0731 | 9.29E−01 | 2.14E+00 | −3.42E−02 | 0.97 |
| Race: Hispanic | 0.8838 | 2.42E+00 | 2.50E+00 | 3.54E−01 | 0.72 |
| Race: Pacific Islander | −16.8824 | 4.66E−08 | 1.12E+05 | −1.51E−04 | 1 |
| Race: White/Caucasian | −1.4232 | 2.41E−01 | 1.58E+00 | −9.00E−01 | 0.37 |
| Donor_age | 0.0189 | 1.02E+00 | 3.46E−02 | 5.45E−01 | 0.59 |
| Age | 0.0238 | 1.02E+00 | 4.54E−02 | 5.25E−01 | 0.6 |

*HLA antibody: dsa: donor specific antigen, reference; ndsa: non dsa antibody; n: no antibody
Induction type: LD: Lymphocyte Depletion, reference; LND: Lymphocyte Non-Depletion; None: No Induction
*The reference for Race: Asian
Likelihood ratio test = 32.1 on 24 df, p = 0.123 n = 135, number of events = 10

TABLE 9

Validation of the GoCAR gene set in other kidney transplant cohorts.

| Data Set | Genechip/ Platform | Sample Size | Outcome | AUC | Ref. |
|---|---|---|---|---|---|
| Dataset 1 | Affymetrix U133 Plus 2.0 | 282 | Allograft loss | 0.83 | 9 |
| Dataset 2 | Affymetrix U133 Plus 2.0 | 24 | CADI | 0.972 | 10 |

REFERENCES

1. Meier-Kriesche H U, Schold J D, Srinivas T R, Kaplan B. Lack of improvement in renal allograft survival despite a marked decrease in acute rejection rates over the most recent era. American journal of transplantation: official journal of the American Society of Transplantation and the American Society of Transplant Surgeons 2004; 4:378-83.
2. Wolfe R A, Roys E C, Merion R M. Trends in organ donation and transplantation in the United States, 1999-2008. American journal of transplantation: official journal of the American Society of Transplantation and the American Society of Transplant Surgeons 2010; 10:961-72.
3. Nankivell B J, Borrows R J, Fung C L, O'Connell P J, Allen R D, Chapman J R. The natural history of chronic allograft nephropathy. N Engl J Med 2003; 349:2326-33.
4. Yilmaz S, McLaughlin K, Paavonen T, et al. Clinical predictors of renal allograft histopathology: a comparative study of single-lesion histology versus a composite, quantitative scoring system. Transplantation 2007; 83:671-6.
5. Yilmaz S, Tomlanovich S, Mathew T, et al. Protocol core needle biopsy and histologic Chronic Allograft Damage Index (CADI) as surrogate end point for long-term graft survival in multicenter studies. Journal of the American Society of Nephrology: JASN 2003; 14:773-9.
6. Solez K, Colvin R B, Racusen L C, et al. Banff 07 classification of renal allograft pathology: updates and future directions. American journal of transplantation: official journal of the American Society of Transplantation and the American Society of Transplant Surgeons 2008; 8:753-60.
7. Irizarry R A, Bolstad B M, Collin F, Cope L M, Hobbs B, Speed T P. Summaries of Affymetrix GeneChip probe level data. Nucleic acids research 2003; 31:e15.
8. Johnson W E, Li C, Rabinovic A. Adjusting batch effects in microarray expression data using empirical Bayes methods. Biostatistics 2007; 8:118-27.
9. Subramanian A, Tamayo P, Mootha V K, et al. Gene set enrichment analysis: a knowledge-based approach for interpreting genome-wide expression profiles. Proceedings of the National Academy of Sciences of the United States of America 2005; 102:15545-50.
10. Einecke G, Reeve J, Sis B, et al. A molecular classifier for predicting future graft loss in late kidney transplant biopsies. The Journal of clinical investigation 2010; 120:1862-72.
11. Naesens M, Khatri P, Li L, et al. Progressive histological damage in renal allografts is associated with expression of innate and adaptive immunity genes. Kidney international 2011; 80:1364-76.
12. Park W D, Griffin M D, Cornell L D, Cosio F G, Stegall M D. Fibrosis with inflammation at one year predicts transplant functional decline. J Am Soc Nephrol 2010; 21:1987-97.
13. Isoniemi H, Taskinen E, Hayry P. Histological chronic allograft damage index accurately predicts chronic renal allograft rejection. Transplantation 1994; 58:1195-8.
14. Cosio F G, Grande J P, Wadei H, Larson T S, Griffin M D, Stegall M D. Predicting subsequent decline in kidney allograft function from early surveillance biopsies. American journal of transplantation: official journal of the American Society of Transplantation and the American Society of Transplant Surgeons 2005; 5:2464-72.
15. Stegall M D, Park W D, Larson T S, et al. The histology of solitary renal allografts at 1 and 5 years after transplantation. American journal of transplantation: official journal of the American Society of Transplantation and the American Society of Transplant Surgeons 2011; 11:698-707.
16. Mannon R B, Matas A J, Grande J, et al. Inflammation in areas of tubular atrophy in kidney allograft biopsies: a potent predictor of allograft failure. American journal of transplantation: official journal of the American Society of Transplantation and the American Society of Transplant Surgeons 2010; 10:2066-73.
17. Hayry P, Paavonen T, Taskinen E, et al. Protocol core needle biopsy and histological chronic allograft damage index as surrogate endpoint for Long-Term graft survival. Transplant Proc 2004; 36:89-91.
18. Seron D, Moreso F, Bover J, et al. Early protocol renal allograft biopsies and graft outcome. Kidney Int 1997; 51:310-6.
19. Seron D, Moreso F, Fulladosa X, Hueso M, Carrera M, Grinyo J M. Reliability of chronic allograft nephropathy diagnosis in sequential protocol biopsies. Kidney Int 2002; 61:727-33.
20. Nankivell B J, Fenton-Lee C A, Kuypers D R, et al. Effect of histological damage on long-term kidney transplant outcome. Transplantation 2001; 71:515-23.
21. Furness P N, Taub N, Assmann K J, et al. International variation in histologic grading is large, and persistent feedback does not improve reproducibility. Am J Surg Pathol 2003; 27:805-10.
22. El-Zoghby Z M, Stegall M D, Lager D J, et al. Identifying specific causes of kidney allograft loss. American journal of transplantation: official journal of the American Society of Transplantation and the American Society of Transplant Surgeons 2009; 9:527-35.
23. Chapman J R. Do protocol transplant biopsies improve kidney transplant outcomes? Curr Opin Nephrol Hypertens 2012; 21:580-6.
24. Shishido S, Asanuma H, Nakai H, et al. The impact of repeated subclinical acute rejection on the progression of chronic allograft nephropathy. J Am Soc Nephrol 2003; 14:1046-52.
25. Kurtkoti J, Sakhuja V, Sud K, et al. The utility of 1- and 3-month protocol biopsies on renal allograft function: a randomized controlled study. American journal of transplantation: official journal of the American Society of Transplantation and the American Society of Transplant Surgeons 2008; 8:317-23.
26. Rush D, Nickerson P, Gough J, et al. Beneficial effects of treatment of early subclinical rejection: a randomized study. J Am Soc Nephrol 1998; 9:2129-34.
27. Rush D, Arlen D, Boucher A, et al. Lack of benefit of early protocol biopsies in renal transplant patients receiving TAC and MMF: a randomized study. American jour- 28. Scherer A, Gwinner W, Mengel M, et al. Transcriptome changes in renal allograft protocol biopsies at 3 months precede the onset of interstitial fibrosis/tubular atrophy (IF/TA) at 6 months. Nephrology, dialysis, transplantation: official publication of the European Dialysis and Transplant Association—European Renal Association 2009; 24:2567-75.

29. Schwarz A, Gwinner W, Hiss M, Radermacher J, Mengel M, Haller H. Safety and adequacy of renal transplant protocol biopsies. American journal of transplantation: official journal of the American Society of Transplantation and the American Society of Transplant Surgeons 2005; 5:1992-6.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description. Patents, patent applications, publications, product descriptions, and protocols are cited throughout this application, the disclosures of which are incorporated herein by reference in their entireties for all purposes.

What is claimed is:

1. A method for treating a human renal allograft recipient at risk for chronic allograft damage or interstitial fibrosis and tubular atrophy (IF/TA) comprising the steps of:
   (a) identifying a human renal allograft recipient as being at risk for chronic allograft damage or IF/TA upon detection of transcription levels in a tissue specimen from the renal allograft recipient of a preselected gene signature set which are higher than the transcription levels of the preselected gene signature set in a renal allograft tissue control sample obtained from a subject that did not develop chronic allograft damage or IF/TA, said transcription levels obtained by
      i. synthesizing cDNA from mRNA isolated from a biopsy specimen obtained from said renal allograft recipient, and
      ii. detecting the transcription levels of the preselected gene signature set in the cDNA, wherein said gene signature set comprises the genes KLHL13, KAAG1, MET, SPRY4, SERINC5, CHCHD10, FJX1, WNT9A, RNF149, ST5, TGIF1, RXRA and ASB15; and
   (b) administering to the human renal allograft recipient having higher transcription levels of the preselected gene signature set an effective amount for treating chronic allograft damage, of an anti-fibrotic agent, an immunosuppressive agent, or both.

2. The method of claim 1 which comprises detecting the transcription levels of said preselected gene signature set of step (a) with RT-PCR analysis.

3. The method of claim 1 which comprises detecting the transcription levels of said preselected gene signature set of step (a) with Nanostring analysis.

4. The method of claim 1 which comprises detecting the transcription levels of said preselected gene signature set of step (a) with $RNA_{SEQ}$ analysis.

5. The method of claim 1 wherein said anti-fibrotic agent is selected from the group consisting of Pirfenidone, relaxin, Bone morphogenetic protein 7 (BMP-7) and Hepatic growth factor (HGF).

6. The method of claim 1 wherein said immunosuppressive agent is selected from the group consisting of a calcineurin inhibitor (CNI), prednisone, mycophenolate mofeti, belatacept, Mycophenolate Sodium and Azathioprine.

7. The method of claim 6 wherein the CNI is cyclosporine or tacrolimus.

8. The method of claim 1 wherein said renal allograft recipient is suffering from allograft rejection.

9. The method of claim 8 wherein said allograft recipient is suffering from acute cellular rejection.

10. The method of claim 8 wherein said allograft recipient is suffering from subcellular rejection.

11. The method of claim 1 which comprises detecting the transcription levels of said preselected gene signature set of step (a) with MiSeq analysis.

* * * * *

UNITED STATES PATENT AND TRADEMARK OFFICE
CERTIFICATE OF CORRECTION

| | | |
|---|---|---|
| PATENT NO. | : 11,674,181 B2 | |
| APPLICATION NO. | : 17/164607 | |
| DATED | : June 13, 2023 | |
| INVENTOR(S) | : Barbara Murphy, Weijia Zhang and Philip J. O'Connell | |

It is certified that error appears in the above-identified patent and that said Letters Patent is hereby corrected as shown below:

In the Claims

Column 32, Line 29, in Claim 6:
Delete "mofeti," and insert -- mofetil, --.

Signed and Sealed this
Eighth Day of August, 2023

Katherine Kelly Vidal
*Director of the United States Patent and Trademark Office*